(12) United States Patent
Ahn

(10) Patent No.: US 12,186,318 B2
(45) Date of Patent: Jan. 7, 2025

(54) PHARMACEUTICAL COMPOSITION FOR PREVENTING OR TREATING CANCER COMPRISING KSP INHIBITOR AND MITOSIS INHIBITOR

(71) Applicant: KOREA INSTITUTE OF SCIENCE AND TECHNOLOGY, Seoul (KR)

(72) Inventor: Hyung Jun Ahn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 661 days.

(21) Appl. No.: 17/083,895

(22) Filed: Oct. 29, 2020

(65) Prior Publication Data
US 2021/0260063 A1    Aug. 26, 2021

(30) Foreign Application Priority Data

Feb. 25, 2020  (KR) .......................... 10-2020-0023032

(51) Int. Cl.
| | | |
|---|---|---|
| *A61K 31/517* | (2006.01) | |
| *A61K 31/337* | (2006.01) | |
| *A61K 31/404* | (2006.01) | |
| *C12N 15/113* | (2010.01) | |
| *A61K 45/06* | (2006.01) | |

(52) U.S. Cl.
CPC .......... *A61K 31/517* (2013.01); *A61K 31/337* (2013.01); *A61K 31/404* (2013.01); *C12N 15/113* (2013.01); *A61K 45/06* (2013.01)

(58) Field of Classification Search
None
See application file for complete search history.

(56) References Cited

U.S. PATENT DOCUMENTS 4,816,567 A    3/1989  Cabilly et al.
9,006,191 B2 *  4/2015  MacLachlan .......... A61P 43/00
                                                     536/23.1

OTHER PUBLICATIONS

Leary et al., Sensitization of Drug Resistant Cancer Cells: A Matter of Combination Therapy. Cancers, 2018, 10, p. 1-18.*
Emma G. Sturgill et al., "Kinesin-5 inhibitor resistance is driven by kinesin-12," J Cell Biol, 2016, pp. 213-227, vol. 213, No. 2.
Gayathri Chandrasekaran et al., "Hitting the brakes: targeting microtubule motors in cancer," British Journal of Cancer, Jul. 2015, pp. 693-698, vol. 113.
Marvin E. Tanenbaum et al., "Kif15 Cooperates with Eg5 to Promote Bipolar Spindle Assembly," Current Biology, 2009, pp. 1703-1711, vol. 19, No. 20.
Stephanie M. Myers et al., "Recent findings and future directions for interpolar mitotic kinesin inhibitors in cancer therapy," Future Med Chem, 2016, pp. 463-489.
Jinju Lee et al., "KSP siRNA/paclitaxel-loaded PEGylated cationic liposomes for overcoming resistance to KSP inhibitors: Synergistic antitumor effects in drug-resistant ovarian cancer," Journal of Controlled Release, 2020, pp. 184-197, vol. 321, Elsevier B.V.
Hualong Song et al., "Kinesin Spindle Protein (KSP) Inhibitors in Combination with Chemotherapeutic Agents for Cancer Therapy," CHEMMEDCHEM, 2013, pp. 1736-1749, vol. 8.
Korean Office Action for KR Application No. 10-2020-0023032 mailed on Oct. 27, 2021, citing the above reference(s).

* cited by examiner

*Primary Examiner* — Po-Chih Chen
(74) *Attorney, Agent, or Firm* — CANTOR COLBURN LLP

(57) ABSTRACT

The present invention relates to a method of treating a cancer including administering a pharmaceutical composition to an individual suspected to have the cancer excluding humans in a pharmaceutically effective amount, where the pharmaceutical composition comprises an agent capable of inhibiting expression of kinesin spindle protein (KSP) and a mitosis inhibitor.

5 Claims, 31 Drawing Sheets

Specification includes a Sequence Listing.

FIG. 2I

| siKSP (nM) \ PTX (nM) | 0 | 10 | 100 | 500 | 1000 | 1500 | 2000 |
|---|---|---|---|---|---|---|---|
| 0 | 0 | -1 | -3 | 1 | 11 | 17 | 21 |
| 10 | 3 | 10 | 11 | 15 | 18 | 22 | 29 |
| 50 | 10 | 21 | 31 | 34 | 44 | 54 | 61 |
| 100 | 14 | 22 | 30 | 36 | 38 | 53 | 60 |

Observed inhibition (%)

FIG. 2J

| siKSP (nM) | 0 | 10 | 100 | 500 | 1000 | 1500 | 2000 |
|---|---|---|---|---|---|---|---|
| 0 | 0 | -1 | -3 | 1 | 11 | 17 | 21 |
| 10 | 3 | 3 | 1 | 4 | 14 | 19 | 24 |
| 50 | 10 | 10 | 8 | 11 | 21 | 25 | 29 |
| 100 | 14 | 13 | 11 | 15 | 24 | 28 | 32 |

Expected inhibition (%)

FIG. 2K

| siKSP (nM) | | | | | | | |
|---|---|---|---|---|---|---|---|
| 0 | 0 | 0 | 0 | 0 | 0 | 0 | 0 |
| 10 | 0 | 7 | 10 | 11 | 4 | 3 | 6 |
| 50 | 0 | 12 | 23 | 22 | 23 | 29 | 32 |
| 100 | 0 | 8 | 18 | 21 | 14 | 25 | 28 |

Excess over Bliss independence (Bliss sum = 296)

```
                       SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: siRNA

<400> SEQUENCE: 1
cugaagaccu gaagacaaud tdt                                           23

<210> SEQ ID NO 2
<211> LENGTH: 23
<212> TYPE: DNA
<213> ORGANISM: Artificial Sequence
<220> FEATURE:
<223> OTHER INFORMATION: siRNA

<400> SEQUENCE: 2
auugucuuca ggucuucagd tdt                                           23

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
ggcgtcgcag ccaaattcgt c                                             21
```

```
<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgccagtttg gccatacgca                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
agagctacga gctgcctgac                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
agcactgtgt tggcgtacag                                               20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ctctcacagt tgaatgtcct tg                                            22

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ctccttgtca gcagaatgaa g                                             21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
acgagacgcc tggttactat c                                             21

<210> SEQ ID NO 10
<211> LENGTH: 25
<212> TYPE: DNA
<213> ORGANISM: Artificial Sequence
<220> FEATURE:
<223> OTHER INFORMATION: primer
```

```
<400> SEQUENCE: 10
gctcatcaat aacagaccca tttac                                              25
```

PHARMACEUTICAL COMPOSITION FOR PREVENTING OR TREATING CANCER COMPRISING KSP INHIBITOR AND MITOSIS INHIBITOR

CROSS-REFERENCE TO RELATED APPLICATION

The present application claims priority to/from and the benefit of Korean Application No. 10-2020-0023032 filed on Feb. 25, 2020, which is incorporated herein by reference in its entirety.

SEQUENCE LISTING

The present application contains a Sequence Listing which has been submitted electronically in ASCII format and is incorporated herein by reference in its entirety. Said ASCII copy, created on Oct. 29, 2020, is named "8N30101.TXT" and is 4,096 bytes in size. The Sequence Listing does not go beyond the disclosure of this application as filed.

TECHNICAL FIELD

The present invention relates to a pharmaceutical composition for preventing or treating a cancer, which includes a kinesin spindle protein (KSP) inhibitor and a mitosis inhibitor, and more particularly, to a pharmaceutical composition for preventing or treating a cancer, which includes an agent capable of inhibiting expression of KSP and a mitosis inhibitor such that a substitution effect for KSP occurring when KSP is inhibited is also inhibited; a method of treating a cancer using the pharmaceutical composition; a pharmaceutical composition for preventing or treating a cancer resistant to a cancer therapeutic agent; and a method of treating a cancer resistant to a cancer therapeutic agent using the pharmaceutical composition.

BACKGROUND ART

A cancer (malignant tumor) is a major disease showing the highest mortality rate in modern society and no breakthrough treatment therefor has been developed yet despite extensive research to date. Although treatment using chemotherapy such as anti-cancer drugs has been effective for cancer treatment to a certain extent, a lot of research on cancer treatment is required due to various mechanisms of cancer outbreak and occurrence of resistance to anti-cancer drugs.

Although limited but positive treatment outcomes such as increases in treatment rates and functional preservation have been achieved in recent decades with the development of diagnostic and therapeutic techniques, five-year survival rates from many progressive cancers are maintained in the range of 5% to 50%. Cancer is characterized by aggressive invasion, lymph node metastasis, distant metastasis, and recurrence of a secondary cancer, and survival rates from some cancers have not significantly been changed for the past 20 years despite various studies and treatments. Recently, attempts to enhance therapeutic effects on cancers via molecular biological approaches have been increased, and research for target treatment related to proliferation, metastasis, and apoptosis of cancers has been actively conducted.

Paclitaxel, a known diterpenoid-based anti-cancer drug, is a mitosis inhibitor acting on cytoskeletons (microtubules). Paclitaxel is known to inhibit division of cancer cells by suppressing a mitotic spindle assembly (MSA), resulting in apoptosis of cancer cells. In particular, paclitaxel is known to have therapeutic effects on a breast cancer and a pancreatic cancer. As the mechanism of the action of paclitaxel has been identified, extensive research has been performed for developing anti-cancer drugs using a protein exhibiting an MSA-inhibiting effect. As part of such research, it has been found that anti-cancer effects may be obtained by inhibiting mitosis of cancer cells by inhibiting a kinesin spindle protein (KSP) involved in a bipolar spindle assembly (BSA) which is a type of MSA, and accordingly, various anti-cancer drugs inhibiting KSP have been developed.

However, such anti-cancer drugs inhibiting KSP could not obtain significant results in clinical trials (Chandrasekaran G, et al., Br J Cancer 2015, 113, 693-8; Myers S M, Collins I, Future Med Chem 2016, 8, 463-89). It has been revealed that this is because Kif15, which is known as a different endogenous kinesin, replaces the function of the inhibited KSP when KSP is inhibited (Tanenbaum M E, et al., Curr Biol 2009, 19, 1703-11). In fact, it has been confirmed that a KSP inhibitor has excellent anti-cancer effects on HeLa cancer cells in which the expression of Kif15 is inhibited, and therefore, functional relationship between KSP and Kif15 has been proven (Sturgill E G, et al., J Cell Biol 2016, 213, 213-27). Therefore, in order to develop anti-cancer drugs including a KSP inhibitor as an active ingredient, it is expected that the action and effects of Kif15 replacing the function of KSP should be inhibited. However, research therefor has not been reported yet.

Under such backgrounds, as a result of intensive efforts to develop anti-cancer drugs including a KSP inhibitor as an active ingredient and capable of inhibiting the action and effects of Kif15 that replaces the function of KSP, the present inventors have found that the action and effects of Kif15 replacing the function of KSP is inhibited by treatment with an mitosis inhibitor together with an agent capable of inhibiting expression of KSP, thereby completing the present invention.

DESCRIPTION OF EMBODIMENTS

Technical Problem

A main object of the present invention is to provide a pharmaceutical composition for preventing or treating a cancer, comprising an agent, which is capable of inhibiting expression of KSP, and a mitosis inhibitor.

Another object of the present invention is to provide a method of treating a cancer using the pharmaceutical composition.

Still another object of the present invention is to provide a pharmaceutical composition for preventing or treating a cancer resistant to a cancer therapeutic agent.

Still another object of the present invention is to provide a method of treating a cancer resistant to a cancer therapeutic agent using the pharmaceutical composition.

Solution to Problem

While performing intensive efforts to develop anti-cancer drugs including an agent capable of inhibiting expression of kinesin spindle protein (KSP) as an active ingredient and capable of inhibiting that the action and effects of Kif15 that substitutes for the function of KSP, the present inventors have found that cytoskeletons (microtubules) are associated with the mobility of Kif15 and studied the effects of paclitaxel on Kif15 based on the fact that the cytoskeleton is directly associated with anti-cancer mechanism and action of paclitaxel, which is one of the mitosis inhibitors. As a result, it was confirmed that paclitaxel inhibits the function of Kif15. Therefore, it was confirmed that an anti-cancer effect of inhibiting the action of KSP without a substitution effect for KSP may be obtained when a composite preparation including an agent, which is capable of inhibiting the expression of KSP, and a mitosis inhibitor is used.

Such anti-cancer drugs inhibiting the action of KSP without a substitution effect for KSP have not been reported prior to the present invention and was identified by the present inventors for the first time.

An aspect of the present invention to achieve the above-described objects provides a pharmaceutical composition for preventing or treating a cancer including an agent, which is capable of inhibiting expression of KSP, and a mitosis inhibitor.

As used herein, the term "kinesin spindle protein (KSP)", also known as Eg5, HsEg5, KNSL1, and KIF11, refers to a kinesin-like motor protein essential for activating bipolar mitosis spindles and is known to be activated for a short period of time while cell division is performed. When the activity of KSP is inhibited, cell division is stopped, finally resulting in apoptosis. An amino acid sequence of the KSP or a nucleotide sequence of a gene encoding the same may be obtained from known database such as GenBank database of The National Center for Biotechnology Information (NCBI, e.g., GenBank No. NT_037436.4). However, any variant in which part of the known amino acid sequences is modified by methods such as an addition, substitution, deletion, or the like may also be within the range of KSP provided by the present invention as long as the variant is available as a target for treatment of cancer cells in the same way as KSP.

As used herein, the term "agent capable of inhibiting expression" broadly includes not only a substance capable inhibiting production of a transcript or protein that are generated by expression of a gene but also a substance capable of inhibiting the activity of the expressed transcript or protein.

In the present invention, examples of the agent used in the present invention include a transcription factor inhibiting a KSP gene at the transcriptional level by binding to the gene; a short interfering RNA or antisense oligonucleotide, such as miRNA, siRNA, and shRNA, which inactivates transcripts (mRNAs) transcribed and synthesized by the KSP gene by binding to the transcripts; and an aptamer or antibody capable of binding to the KSP gene or KSP expressed therefrom.

As used herein, the term "short interfering RNA" refers to a double-stranded RNA capable of inducing RNAi that inhibits the activity of a gene.

In the present invention, the short interfering RNA may be miRNA, siRNA, shRNA, or the like, which may inhibit the expression of KSP. Furthermore, the short interfering RNA may be any short interfering RNA as long as it inactivates mRNA of KSP. For example, the short interfering RNA may be either siRNA obtained by chemical synthesis, biochemical synthesis, or in vivo synthesis, or double-stranded RNA consisting of at least 10 base pairs, which results from in vivo degradation of double-stranded RNA consisting of about 40 bases or more; preferably, the short interfering RNA may be an siRNA including a nucleotide sequence consisting of SEQ ID NOS: 1 and 2.

The short interfering RNA may be composed of a sequence having at least about 70%, preferably at least 75%, more preferably at least 80%, even more preferably at least 85%, even more preferably at least 90%, particularly preferably at least 95%, and most preferably at least 100%, homology with a portion of the nucleic acid sequence of RNA of KSP. In addition, RNA including the double-stranded portion, or a modified product thereof, may also be used in the present invention. The sequence portion having the homology may generally include at least 15 nucleotides, preferably about at least 19 nucleotides, more preferably at least 20 nucleotides, and even more preferably at least 21 nucleotides.

As used herein, the term "antisense oligonucleotide" refers to DNA, RNA, or a derivative thereof, which contains a complementary nucleic acid sequence to a particular mRNA sequence and binds to the particular sequence in the mRNA, thereby acting to inhibit translation of the mRNA into a protein.

In the present invention, a sequence of the antisense oligonucleotide may be understood as a DNA or RNA sequence which is complementary to the mRNA of KSP and is able to bind to the mRNA. The antisense oligonucleotide may inhibit essential activities with respect to translation of the mRNA of KSP, translocation into cytoplasm, maturation, or all other biological functions. A length of the antisense oligonucleotide may be 6 to 100 nucleotides, preferably 8 to 60 nucleotides, and more preferably 10 to 40 nucleotides.

As used herein, the term "aptamer" refers to a nucleic acid molecule having a binding activity to a particular target molecule.

In the present invention, the aptamer may be understood as a substance binding to a KSP gene or KSP, thereby inhibiting the activity of the gene or protein.

The aptamer of the present invention may be RNA, DNA, a modified nucleic acid, or a mixture thereof, and may be in a linear or circular form. A length of the aptamer of the present invention is not particularly limited, but may generally be 15 to 200 nucleotides, for example, 100 nucleotides or less, 80 nucleotides or less, or 45 nucleotides or less. As the length of the aptamer decreases, the aptamer has various advantages in that it is chemically synthesized and mass-produced more easily, enabling more cost-effective production thereof, chemically modified easily, has higher in vivo stability, and lower toxicity.

As used herein, the term "antibody" refers to a substance which is produced by stimulation of an antigen in the immune system to specifically bind to a particular antigen, resulting in inducing an antigen-antibody reaction.

In the present invention, the antibody may be understood as an antibody specifically binding to KSP to inhibit the activity of the KSP, and may be a polyclonal antibody, a monoclonal antibody, or an antibody including a single chain variable region fragment (scFv).

The antibody specifically binding to the KSP provided according to the present invention may be prepared by a method well-known in the art, for example, a cell fusion method (Kohler and Milstein, European Journal of Immunology, 6:511-519 1976)), a recombinant DNA method (U.S. Pat. No. 4,816,567), or a phage antibody library method (Clackson et al, Nature, 352:624-628 (1991) and Marks et al, J. Mol. Biol., 222:58, 1-597 (1991)).

As used herein, the term "mitosis inhibitor" refers to an agent that blocks mitosis of cancer cells resulting in exhibiting an anti-cancer activity and inhibiting the function of Kif15 that substitutes for the function of KSP.

In the present invention, the mitosis inhibitor is not particularly limited but examples thereof may include paclitaxel, Kif15-IN-1 (quinazolinedione), and GW108X (oxindole).

In particular, paclitaxel belongs to the type of chemotherapeutic drugs called plant alkaloids, and refers to a diterpenoid-based anti-cancer substance first isolated from the bark of a yew tree. Paclitaxel acts as a mitosis inhibitor targeting a cytoskeleton (microtubule) and is approved by the U.S. Food and Drug Administration (FDA) for the treatment of an ovarian cancer, a breast cancer, a head and neck cancer, Kaposi's sarcoma, and a non-small cell lung cancer. Extensive research has been actively conducted for ongoing indications (Alzheimer's disease and rheumatoid arthritis) and treatment methods thereof.

As used herein, the term "cancer" refers to a condition in which abnormal cells, which have lost the ability to regulate cell growth and should be eliminated, excessively proliferate and invade adjacent tissue and organs to form lumps, thereby destroying or deforming the existing structure. The term "cancer" is used interchangeably with malignant tumor.

In the present invention, the types of cancer are not particularly limited as long as they may be treated by inhibiting mitosis thereof, and examples of the cancer may include a pancreatic cancer, a breast cancer, a prostate cancer, a brain tumor, a head and neck carcinoma, melanoma, myeloma, leukemia, lymphoma, a liver cancer, a gastric cancer, a colon cancer, a bone cancer, an uterine cancer, an ovarian cancer, a rectal cancer, an esophageal cancer, a small intestine cancer, an anal rectal cancer, fallopian tube carcinoma, endometrial carcinoma, cervical carcinoma, vaginal carcinoma, vulvar carcinoma, Hodgkin's disease, a bladder cancer, a kidney cancer, an urinary tract cancer, a renal cell cancer, renal pelvic carcinoma, and central nervous system tumor. Another example may include a breast cancer, an ovarian cancer, etc.

As used herein, the term "prevention" refers to any action resulting in inhibition or delay of the onset of a cancer by administering the pharmaceutical composition according to the present invention.

As used herein, the term "treatment" refers to any action resulting in improvement or beneficial alternation of symptoms of an individual suspected or confirmed to have a cancer by administering the pharmaceutical composition.

The pharmaceutical composition for preventing or treating a cancer, which is provided by the present invention, exhibits an effect different from that of conventional anti-cancer drugs in that a substitution effect of Kif15 for KSP, which is induced by conventional agents capable of inhibiting the expression of KSP, is inhibited without directly inhibiting the expression of Kif15, and low anti-cancer activity of paclitaxel shown in drug-resistant cancer tissue is improved.

According to an embodiment of the present invention, provided is a preparation including: KSP siRNA (an agent capable of inhibiting expression of KSP) entrapped using interactions between positive charges of DC-Chol lipids constituting a PEGylated cationic liposome and negative charges of the KSP siRNA; and paclitaxel (mitosis inhibitor) having hydrophobicity and entrapped using a hydrophobic environment of a phospholipid bilayer constituting the liposome. The obtained preparation is in the form of a PEGylated liposome including KSP siRNA (SEQ ID NOS: 1 and 2) and paclitaxel in which paclitaxel is contained inside a lipid layer constituting the liposome and the lipid layer containing paclitaxel entraps the KSP siRNA by surrounding KSP siRNA (FIG. 1B).

According to another embodiment, paclitaxel shows a Kif15 inhibiting effect similar to a Kif15 inhibitor (FIG. 2F); although paclitaxel monotherapy or KSP siRNA monotherapy shows very low apoptosis-inducing efficiencies in HeyA8-MDR carcinoma (FIG. 2G), a KSP siRNA/PTX-loaded liposome transmitter has a far higher apoptosis-inducing efficiency in vitro than the paclitaxel monotherapy or the KSP siRNA monotherapy (FIGS. 2H to 2M); and such pharmacological effects were proven not only in cell lines (in vitro) but also in various animal models (in vivo) in the same manner or a similar manner (FIGS. 3A to 5H).

The pharmaceutical composition of the present invention may include the extract in an amount of 0.001 to 80 wt %, specifically 0.001 to 70 wt %, more specifically 0.001 to 60 wt % based on a total weight of the composition, but is not limited thereto.

In addition, the pharmaceutical composition may further include pharmaceutically acceptable carriers, excipients, or diluents which are commonly used in the preparation of pharmaceutical compositions. The carriers may include non-naturally occurring carriers. Examples of the carriers, excipients, and diluents may include lactose, dextrose, sucrose, sorbitol, mannitol, xylitol, erythritol, maltitol, starch, Acacia rubber, alginate, gelatin, calcium phosphate, calcium silicate, cellulose, methyl cellulose, amorphous cellulose, polyvinyl pyrrolidone, water, methyl hydroxyl benzoate, propyl hydroxyl benzoate, talc, magnesium stearate, and mineral oils.

Additionally, the pharmaceutical composition may be used in formulations such as tablets, pills, powders, granules, capsules, suspensions, solutions for internal use, emulsions, syrups, sterilized aqueous solutions, non-aqueous solvents, lyophilized preparations, transdermal agents, gels, lotions, ointments, creams, patches, cataplasma agents, pastes, sprays, skin emulsions, skin suspensions, transdermal patches, drug-containing bandages, or suppositories according to the conventional methods. Specifically, the pharmaceutical composition may be formulated with diluents or excipients commonly used in the art, such as fillers, extenders, binders, humectants, disintegrants, surfactants, etc. Solid formulations for oral administration may include tablets, pills, powders, granules, capsules, and the like, but are not limited thereto. Such solid formulations may be prepared by being mixed with at least one excipient, for example, starch, calcium carbonate, sucrose, lactose, gelatin, etc. In addition to simple excipients, lubricants such as magnesium stearate or talc may also be used. Liquid formulations for oral administration may be prepared by adding various excipients, for example, humectants, sweeteners, aromatics, preservatives, etc., in addition to liquid paraffin. Formulations for parenteral administration may include sterilized aqueous solutions, non-aqueous solvents, suspensions, emulsions, lyophilized preparations, and suppositories. The non-aqueous solutions and the suspensions may include propylene glycol, polyethylene glycol, vegetable oil such as olive oil, injectable ester such as ethyloleate, etc. A base for suppositories may include witepsol, macrogol, tween 61, cacao butter, laurin butter, glycerogelatin, etc.

Another aspect of the present invention provides a method of treating a cancer including administering the pharmaceutical composition to an individual suspected to have the cancer excluding humans.

As used herein, the term "administration" refers to introducing the pharmaceutical composition into an individual using any appropriate method.

As used herein, the term "individual" refers to all animals such as mice, rats, and livestock including humans with a cancer or at the risk of developing a cancer. Specific examples thereof may be mammals including humans.

The pharmaceutical composition of the present invention is administered in a pharmaceutically effective amount. The term "pharmaceutically effective amount" refers to an amount sufficient for treatment of diseases at a reasonable benefit/risk ratio applicable to medical treatment, and an effective dose may be determined based on factors including the type of individual, severity of illness, age and gender of the individual, drug activity, and drug sensitivity, administration time, administration route and excretion rate, duration of treatment, factors including drug(s) concurrently used in combination, and other factors well-known in the medical field. For example, the pharmaceutical composition may be administered in a daily dosage of 0.01 to 500 mg/kg, specifically 10 to 100 mg/kg, once per day or in several divided doses per day.

The pharmaceutical composition may be administered alone or in combination with other therapeutic agents, and may be administered sequentially or simultaneously with existing therapeutic agents. In addition, the composition may be administered in a single or multiple dosage form. Considering all the above-described factors, it is important to administer the pharmaceutical composition in a minimum amount that may exhibit a maximum effect without causing side effects. The amount may be readily determined by those skilled in the art.

In addition, the pharmaceutical composition may be administered orally or parenterally (e.g., intravenous, subcutaneous, intraperitoneal or topical administration) depending on the purpose, and the dose may be properly selected by those skilled in the art depending on conditions and body weight of a patient, severity of a disease, formulation of a drug, and administration route and time.

Still another aspect of the present invention provides a pharmaceutical composition for preventing or treating a cancer resistant to a therapeutic agent, and a method of treating a cancer resistant to a cancer therapeutic agent by using the pharmaceutical composition.

According to an embodiment of the present invention, cancer tissue was excised from a patient (having a cancer resistant to a cancer therapeutic agent) who experienced recurrence of adenocarcinoma during chemotherapy of administering paclitaxel (mitosis inhibitor) after a primary debulking surgery of adenocarcinoma. The excised cancer tissue was implanted into a subrenal capsule of the left kidney of a mouse to prepare a drug-resistant PDX model. Thereafter, as a result of administering the pharmaceutical composition including an agent capable of inhibiting expression of KSP and paclitaxel according to the present invention to the drug-resistant PDX model, it was confirmed that a weight of the tumor tissue was significantly decreased when compared to a case administered with the agent capable of inhibiting expression of KSP or paclitaxel alone (FIGS. 5A and 5B).

Therefore, it can be seen that the pharmaceutical composition including an agent, which is capable of inhibiting expression of KSP, and a mitosis inhibitor according to the present invention may also be used to treat a cancer resistant to a cancer therapeutic agent.

In the present invention, the cancer resistant to a cancer therapeutic agent may be a cancer resistant to a cancer therapeutic agent having a mitosis inhibiting activity such as paclitaxel, but is not limited thereto.

Additionally, the method of treating a cancer resistant to a cancer therapeutic agent, which is provided by the present invention, includes administering the pharmaceutical composition to an individual suspected to have the cancer resistant to the cancer therapeutic agent in a pharmaceutically effective amount.

Advantageous Effects of Disclosure

The pharmaceutical composition for preventing or treating a cancer including an agent, which is capable of inhibiting expression of KSP, and a mitosis inhibitor according to the present invention may simultaneously inhibit the expression of KSP and a substitution effect of Kif15 for KSP; may induce synergistic effects on an anti-cancer activity when compared to treatment with the agent capable of inhibiting expression of KSP or the mitosis inhibitor alone; and may also have a therapeutic effect on a cancer resistant to a cancer therapeutic agent having a mitosis inhibiting activity. Accordingly, the pharmaceutical composition of the present invention can be widely used for anti-cancer therapy more efficiently.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2I is a table showing observed inhibition levels of cancer cells according to concentrations of the KSP siRNA-containing PEGylated liposome and paclitaxel in HeyA8-MDR cells when the cells are simultaneously treated therewith.

FIG. 2J is a table showing expected inhibition levels of cancer cells according to concentrations of the KSP siRNA-containing PEGylated liposome and paclitaxel in HeyA8-MDR cells when the cells are simultaneously treated therewith.

FIG. 2K is a table showing differences between the observed inhibition levels and the expected inhibition levels of cancer cells according to concentrations of the KSP siRNA-containing PEGylated liposome and paclitaxel in HeyA8-MDR cells when the cells are simultaneously treated therewith.

BEST MODE

Hereinafter, the present invention will be described in more detail with reference to the following examples. However, these examples are for illustrative purposes only and are not intended to limit the scope of the present invention.

Example 1: Manufacture of Anti-Cancer Preparation Containing KSP siRNA and Paclitaxel Example 1-1: Manufacture of KSP siRNA-Containing Preparation First, a PEGylated DC-Chol/DOPE cationic liposome was prepared using a known thin-film hydration method (Lee J, et al., Theragnosis 2016, 6, 192-203). DC-Chol, DOPE, and mPEG2000-DSPE were mixed in a ratio of 48.75:48.75:2.5 (molar ratio) such that a total weight of the mixture was approximately 300 μg, and chloroform was removed therefrom by lyophilization for 12 hours, thereby preparing a PEGylated liposome in the form of dry lipid film.

Subsequently, a PEGylated liposome into which KSP siRNA is introduced was prepared. Approximately, KSP siRNA consisting of nucleotides of SEQ ID NOS: 1 and 2 and a PBS buffer (containing 5% glucose, 10 mM, pH 7.4) were added to the PEGylated liposome in the dry lipid film form, followed by sonication for 30 seconds and stirring at room temperature for 4 hours to obtain a mixture. Herein, a mixing ratio of the PEGylated liposome and KSP siRNA was set in various ranges (20:1, 40:1, 60:1, 80:1, and 100:1 (w/w)). The obtained mixtures were extrusion-molded three times by applying to a polycarbonate membrane (100 nm) and a mini hand-held extruder (Avanti Polar Lipid, US), and the resultants were sterilized by passing through a sterile filter (0.22 μm), thereby preparing PEGylated liposomes into which KSP siRNA is introduced.

KSP siRNA F: 5'-CUGAAGACCUGAAGACAAUdTdT-3' (SEQ ID NO: 1)
KSP siRNA R: 5'-AUUGUCUUCAGGUC-UUCAGdTdT-3' (SEQ ID NO: 2)

Figure 1A:
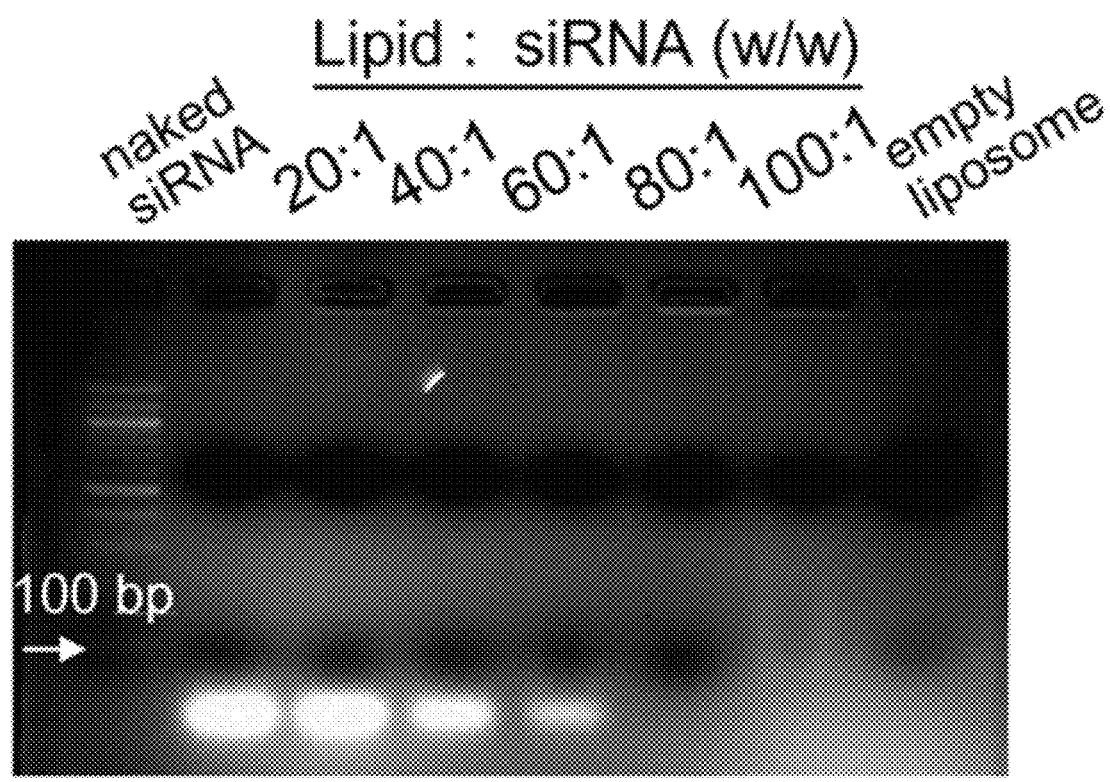
FIG. 1A is an electrophoresis image showing results of comparison among sizes of PEGylated liposomes introduced with KSP siRNA according to mixing ratios of a liposome and KSP siRNA.

Each of the prepared PEGylated liposomes into which KSP siRNA is introduced was electrophoresed to compare sizes of the liposomes (FIG. 1A).

FIG. 1A is an electrophoresis image showing results of comparison among sizes of PEGylated liposomes introduced with KSP siRNA according to mixing ratios of the liposome and KSP siRNA.

As shown in FIG. 1A, it was confirmed that KSP siRNA and the PEGylated liposome form a complex having a high molecular weight when the mixing ratio of PEGylated liposomes to KSP siRNA was from 20:1 to 60:1, but the complex was not formed when the mixing ratio of the PEGylated liposome to KSP siRNA was 80:1 and 100:1.

Example 1-2: Manufacture of Paclitaxel-Containing Preparation

A PEGylated liposome was prepared using the known thin-film hydration method (Lee J, et al., Theragnosis 2016, 6, 192-203). DC-Chol, DOPE, and mPEG2000-DSPE were mixed in a ratio of 48.75:48.75:2.5 (molar ratio) such that a total weight of the mixture was approximately 300 μg to obtain a lipid mixture, and paclitaxel was added to the obtained lipid mixture, thereby obtaining a final mixture. Chloroform was removed from the obtained final mixture by lyophilization for 12 hours to prepare a paclitaxel-containing PEGylated liposome.

Example 1-3: Manufacture of Preparation Containing KSP siRNA and Paclitaxel

5 μg of KSP siRNA consisting of nucleotides of SEQ ID NOS: 1 and 2 and 1 ml of a PBS buffer (including 5% glucose, 10 mM, pH 7.4) were added to the paclitaxel-containing PEGylated liposome obtained in Example 1-2 above, followed by sonication for 30 seconds and stirring at room temperature for 4 hours to obtain a mixture. The obtained mixture was extrusion-molded three times by applying to a polycarbonate membrane (100 nm) and a mini hand-held extruder (Avanti Polar Lipid, US), and then sterilized by passing through a sterile filter (0.22 μm), thereby preparing a PEGylated liposome containing both KSP siRNA and paclitaxel (FIG. 1B).

Figure 1B:
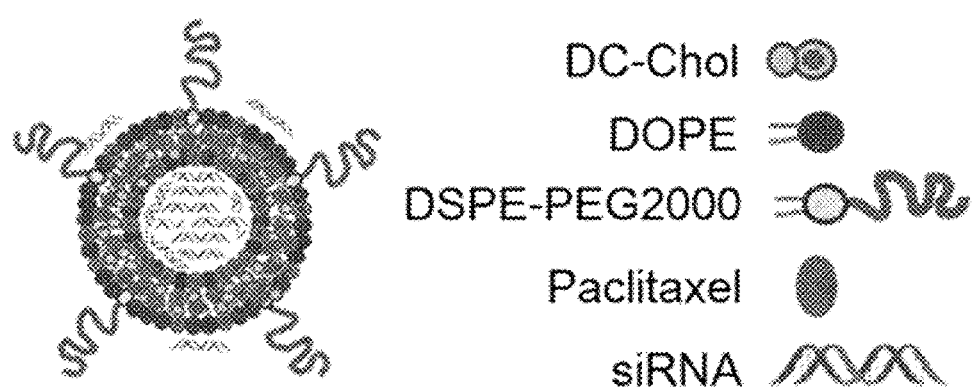
FIG. 1B is a schematic diagram illustrating a shape of a PEGylated liposome containing both KSP siRNA and paclitaxel according to the present invention.

FIG. 1B is a schematic diagram illustrating a shape of a PEGylated liposome containing both KSP siRNA and paclitaxel according to the present invention.

As shown in FIG. 1B, the PEGylated liposome containing both KSP siRNA and paclitaxel provided by the present invention has a structure in which paclitaxel is contained inside a lipid layer and the lipid layer containing paclitaxel surrounds and entraps KSP siRNA.

Figure 1C:
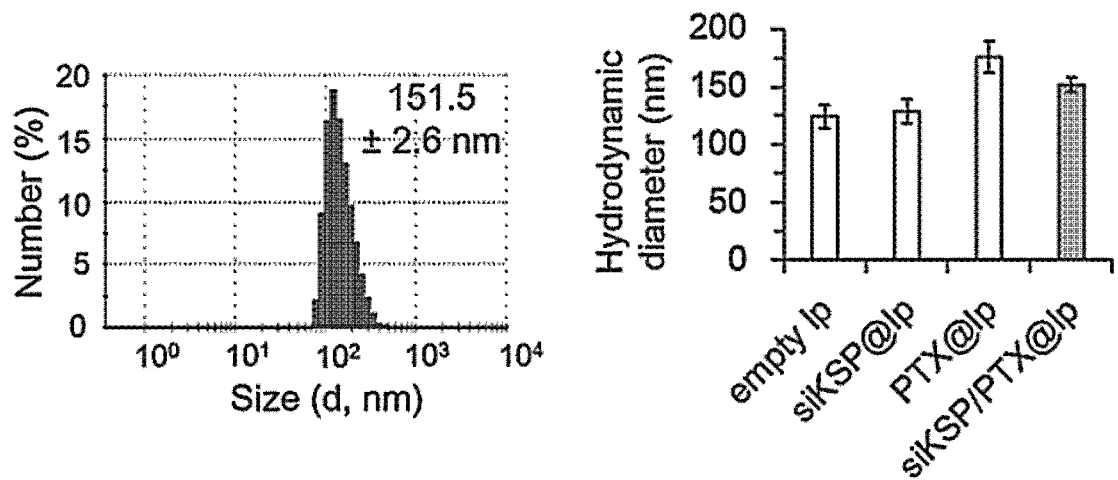
FIG. 1C is a graph illustrating results of comparison among particle sizes of PEGylated liposomes which selectively contain KSP siRNA and paclitaxel.

Example 2: Analysis of Properties of Preparation Containing KSP siRNA and Paclitaxel Example 2-1: Particle Size Particle sizes (hydrodynamic diameters) of the PEGylated liposomes respectively prepared according to Examples 1-1 to 1-3 were measured and compared (FIG. 1C). In this case, a pure PEGylated liposome, which does not contain KSP siRNA and paclitaxel, was used as a control.

FIG. 1C is a graph illustrating results of comparison among particle sizes of the respective PEGylated liposomes which selectively contain KSP siRNA and paclitaxel.

As shown in FIG. 1C, it was confirmed that the PEGylated liposome containing both KSP siRNA and paclitaxel had a particle size of about 151.5 nm which is greater than the particle size of the PEGylated liposome containing only KSP siRNA and smaller than the particle size of the PEGylated liposome containing only paclitaxel.

Example 2-2: Zeta Potential

Figure 1D:
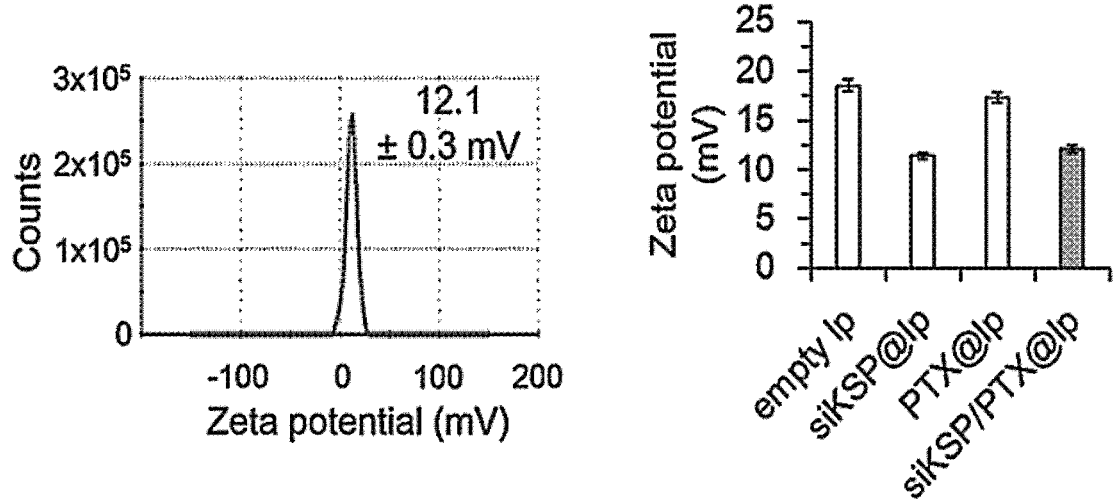
FIG. 1D is a graph illustrating results of comparison among zeta potentials of PEGylated liposomes which selectively contain KSP siRNA and paclitaxel.

Zeta potentials of the PEGylated liposomes respectively prepared according to Examples 1-1 to 1-3 were measured and compared (FIG. 1D). In this case, a pure PEGylated liposome, which does not contain KSP siRNA and paclitaxel, was used as a control.

FIG. 1D is a graph illustrating results of comparison among zeta potentials of the respective PEGylated liposomes which selectively contain KSP siRNA and paclitaxel.

As shown in FIG. 1D, it was confirmed that the PEGylated liposome containing both KSP siRNA and paclitaxel had a zeta potential of about 12.1 mV which is slightly higher than a zeta potential of the PEGylated liposome containing only KSP siRNA and far less than a zeta potential of the PEGylated liposome containing only paclitaxel.

Example 2-3: Shape of Preparation Containing KSP siRNA and Paclitaxel

Figure 1E:
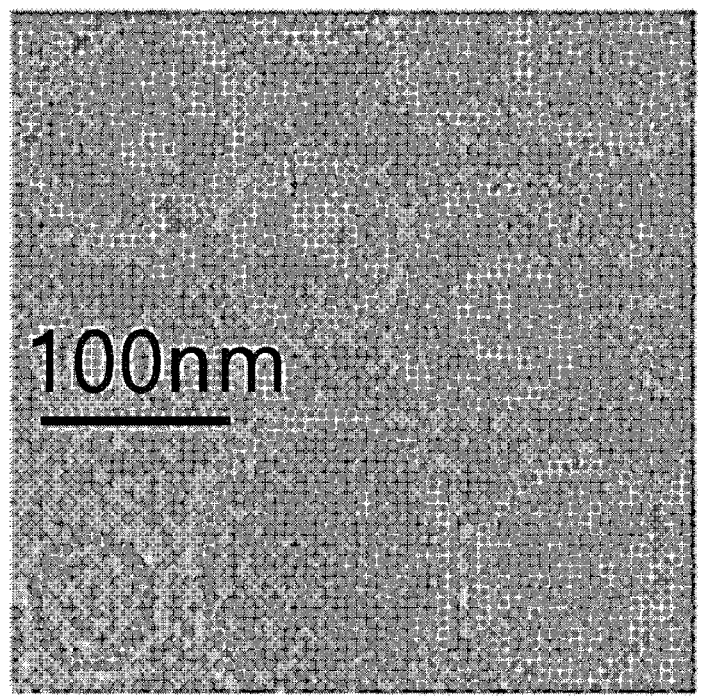
FIG. 1E is a TEM image showing shapes of a PEGylated liposome containing both KSP siRNA and paclitaxel.

Shapes of the PEGylated liposome, which contains both KSP siRNA and paclitaxel and which is prepared in Example 1-3, were observed via transmission electron microscopy (TEM) (FIG. 1E).

FIG. 1E is a TEM image showing shapes of the PEGylated liposome containing both KSP siRNA and paclitaxel.

As shown in FIG. 1E, it was confirmed that the PEGylated liposome containing both KSP siRNA and paclitaxel had a spherical shape in its appearance.

Example 2-4: Cell Permeability of Preparation Containing KSP siRNA and Paclitaxel First, a PEGylated liposome containing both Cy5.5-labeled KSP siRNA (Cy5.5-scKSP) and oregon-labeled paclitaxel (oregon-paclitaxel) was prepared according to the method described in Example 1-3.

Subsequently, HeyA8-MDR cells, which had been cultured in a 12-well plate at a density of $1 \times 10^5$ cells/well using an RPMI-1640 medium (supplemented with 10% FBS and 0.1% gentamicin sulfate), were treated with the PEGylated liposome containing the labeled KSP siRNA and paclitaxel, followed by reaction for 2 hours and washing with a PBS buffer. Thereafter, the cells were immobilized with 4% (w/V) paraformaldehyde, and nuclei thereof were stained with DAPI. Then, a confocal microscope image of the cells was obtained to identify whether the PEGylated liposome containing the labeled KSP siRNA and paclitaxel permeated into the cells (FIG. 1F).

Figure 1F:
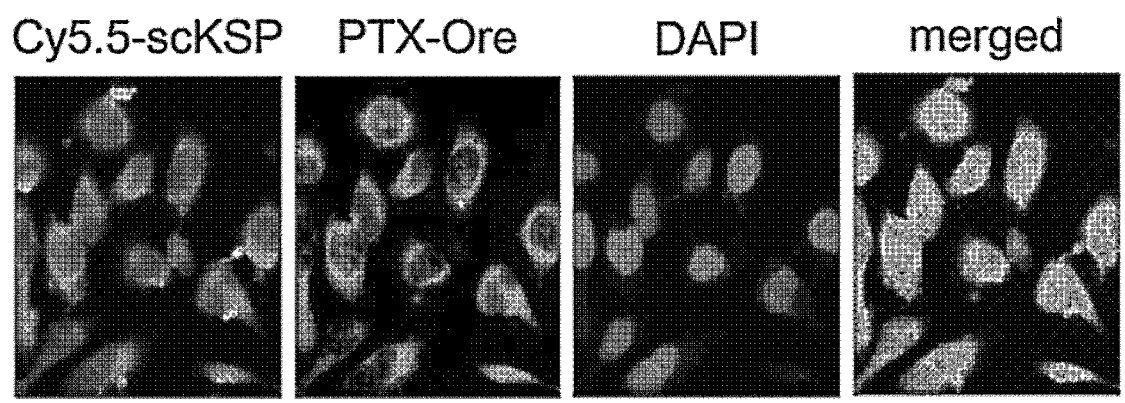
FIG. 1F shows a confocal microscope image of HeyA8-MDR cells treated with a PEGylated liposome containing labeled KSP siRNA and paclitaxel.

FIG. 1F shows a confocal microscope image of HeyA8-MDR cells treated with the PEGylated liposome containing the labeled KSP siRNA and paclitaxel.

As shown in FIG. 1F, it was confirmed that the PEGylated liposome containing both KSP siRNA and paclitaxel permeated into the cells.

Meanwhile, entrapment efficiencies of KSP siRNA and paclitaxel contained in the PEGylated liposomes were calculated using the Cy5.5-labeled KSP siRNA (Cy5.5-scKSP) and the oregon-labeled paclitaxel (oregon-paclitaxel).

First, a standard curve of 'mass vs. fluorescence intensity' for the Cy5.5-KSP siRNA and the oregon-paclitaxel was calculated.

Subsequently, a PEGylated liposome containing KSP siRNA and paclitaxel was prepared using 5 μg of Cy5.5-KSP siRNA, 15 μg of oregon-paclitaxel, and 300 μg of a PEGylated liposome according to the method described in Example 1-3, and fluorescence intensities of Cy5.5 and oregon remaining in the filter were measured using a spectrofluorometer (Appliskan, Thermo Fisher Scientific, USA).

Finally, the measured fluorescence intensities of Cy5.5 and oregon were substituted into the standard curve to calculate the amounts of Cy5.5-KSP siRNA and oregon-paclitaxel.

As a result, it was confirmed that 3.8±0.9 μg of the Cy5.5-KSP siRNA and 9.6±0.3 μg of the oregon-paclitaxel were contained in the thus-prepared PEGylated liposomes containing KSP siRNA and paclitaxel. This indicates that entrapment efficiencies of the Cy5.5-KSP siRNA and oregon-paclitaxel are 75.7±5.7% and 64.3±1.7%, respectively. A composition ratio calculated as a molar ratio was 77:1:2.5 (lipid:siKSP:paclitaxel).

Example 3: Effect of Preparation Containing KSP siRNA and Paclitaxel Under In Vitro Condition Effects and actions of the PEGylated liposome containing KSP siRNA and paclitaxel prepared according to Example 1-3 (hereinafter, referred to as 'KSP siRNA/PTX-liposome') were analyzed in vitro.

Example 3-1: Inhibitory Effect on Expression of KSP at the Gene Level

First, HeyA8-MDR cells, which had been cultured in a 6-well plate at a density of $1 \times 10^5$ cells/well using an RPMI-1640 medium (supplemented with 10% FBS and 0.1% gentamicin sulfate), were treated respectively with PBS (control; 10 μM), a mixture of siKSP and a PEGylated liposome (scKSP@Ip; equivalent to 50 nM siKSP), a KSP siRNA-containing PEGylated liposome (siKSP@Ip; equivalent to 50 nM siKSP), and a KSP siKSP/PTX-liposome (siKSP/PTX@Ip; equivalent to 50 nM siKSP and 2000 nM PTX) for 48 hours, and then the cells were recovered.

Subsequently, total RNA was obtained from each of the recovered cells using an RNeasy mini kit (Qiagen, US), KSP cDNA was synthesized from the obtained total RNA using a TOPscript cDNA synthesis kit (Enzynomics, Korea), and PCR was performed using a StepOne qRT-PCR system (Thermo Fisher scientific) and primers specific to a KSP gene (SEQ ID NOS: 3 and 4) or primers specific to a β-actin gene (SEQ ID NOS: 5 and 6).

```
KSP F:
                                    (SEQ ID NO: 3)
5'-GGCGTCGCAGCCAAATTCGTC-3'

KSP R:
                                    (SEQ ID NO: 4)
5'-TGCCAGTTTGGCCATACGCA-3'

β-actin F:
                                    (SEQ ID NO: 5)
5'-AGAGCTACGAGCTGCCTGAC-3'

β-actin R:
                                    (SEQ ID NO: 6)
5'-AGCACTGTGTTGGCGTACAG-3'
```

Figure 2A:
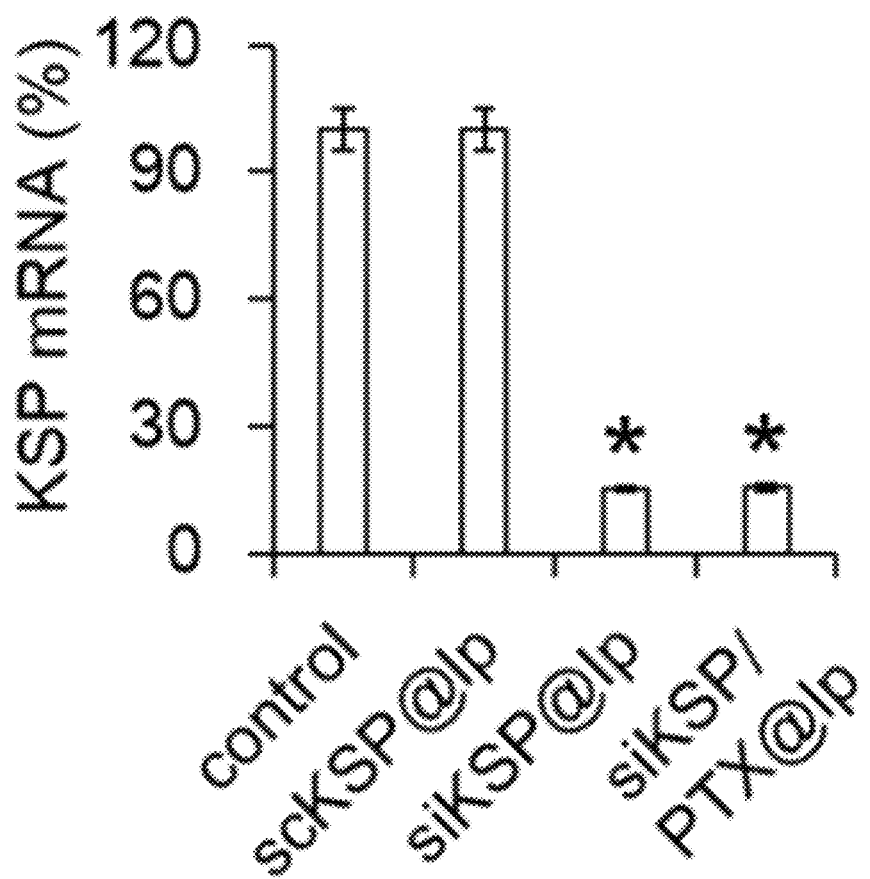
FIG. 2A is a graph illustrating results of comparison among expression levels of a KSP gene in HeyA8-MDR cells showing changes by treatment with a KSP SiRNA/PTX-liposome.

Thereafter, levels of the amplified products obtained from the PCR were measured, and the measured levels were standardized with respect to an expression amount of β-actin, and then relative levels of KSP mRNA were calculated (FIG. 2A).

FIG. 2A is a graph illustrating results of comparison among expression levels of a KSP gene in HeyA8-MDR cells showing changes by treatment with the KSP siRNA/PTX-liposome.

As shown in FIG. 2A, it was confirmed that the expression of a KSP gene was inhibited in cells when the cells were treated with the PEGylated liposome containing siKSP or the PEGylated liposome containing both siKSP and paclitaxel.

Example 3-2: Inhibitory Effect on Expression of KSP at the Protein Level

Figure 2B:
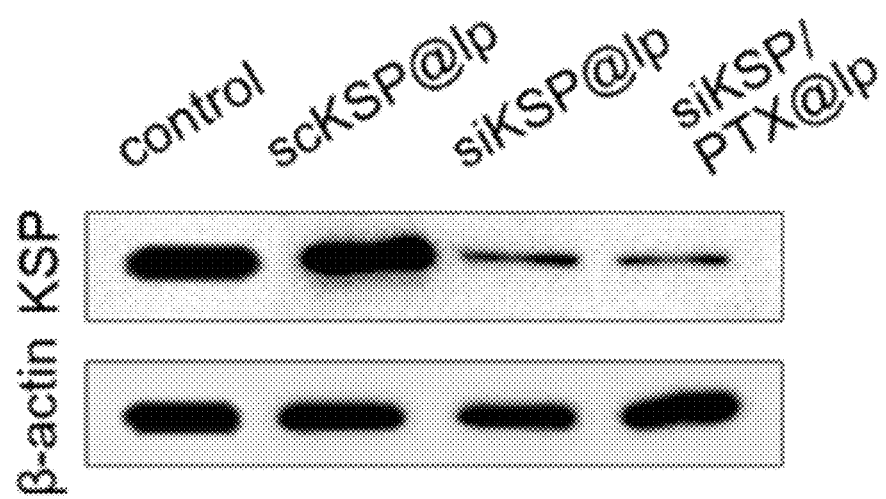
FIG. 2B is a western blot analysis image illustrating results of comparison among KSP levels in HeyA8-MDR cells showing changes by treatment with the KSP siRNA/PTX-liposome.

The cells recovered in Example 3-1 above were analyzed by western blotting using an anti-KSP antibody (FIG. 2B).

FIG. 2B is a western blot analysis image illustrating results of comparison among KSP levels in HeyA8-MDR cells showing changes by treatment with the KSP siRNA/PTX-liposome.

As shown in FIG. 2B, it was confirmed that the KSP protein level was reduced in the cells by treating the cells with the PEGylated liposome containing siKSP or the PEGylated liposome containing both siKSP and paclitaxel.

Example 3-3: Inhibitory Effect on Expression of Kif15 at the Gene Level

First, HeyA8-MDR cells, which has been cultured in a 6-well plate at a density of $1 \times 10^5$ cells/well using an RPMI-1640 medium (supplemented with 10% FBS and 0.1% gentamicin sulfate), were treated respectively with PBS (control; 10 μM), paclitaxel (PTX; equivalent to 2000 nM PTX), a KSP siRNA-containing PEGylated liposome (sikSP@Ip; equivalent to 50 nM siKSP), a paclitaxel-containing PEGylated liposome (PTX@Ip; equivalent to 2000 nM PTX), and a KSP siKSP/PTX-liposome (siKSP/

PTX@Ip; equivalent to 50 nM siKSP and 2000 nM PTX) for 48 hours, and then the cells were recovered.

Subsequently, total RNA was obtained respectively from the recovered cells using an RNeasy mini kit (Qiagen, US), cDNA was synthesized from the obtained total RNA using a TOPscript cDNA synthesis kit (Enzynomics, Korea), and PCR was performed using a StepOne qRT-PCR system (Thermo Fisher scientific) and primers specific to a Kif15 gene (SEQ ID NOS: 7 and 8) or primers specific to a β-actin gene (SEQ ID NOS: 5 and 6).

```
Kif15 F:
                              (SEQ ID NO: 7)
5'-CTCTCACAGTTGAATGTCCTTG-3'

Kif15 R:
                              (SEQ ID NO: 8)
5'-CTCCTTGTCAGCAGAATGAAG-3'
```

Figure 2C:
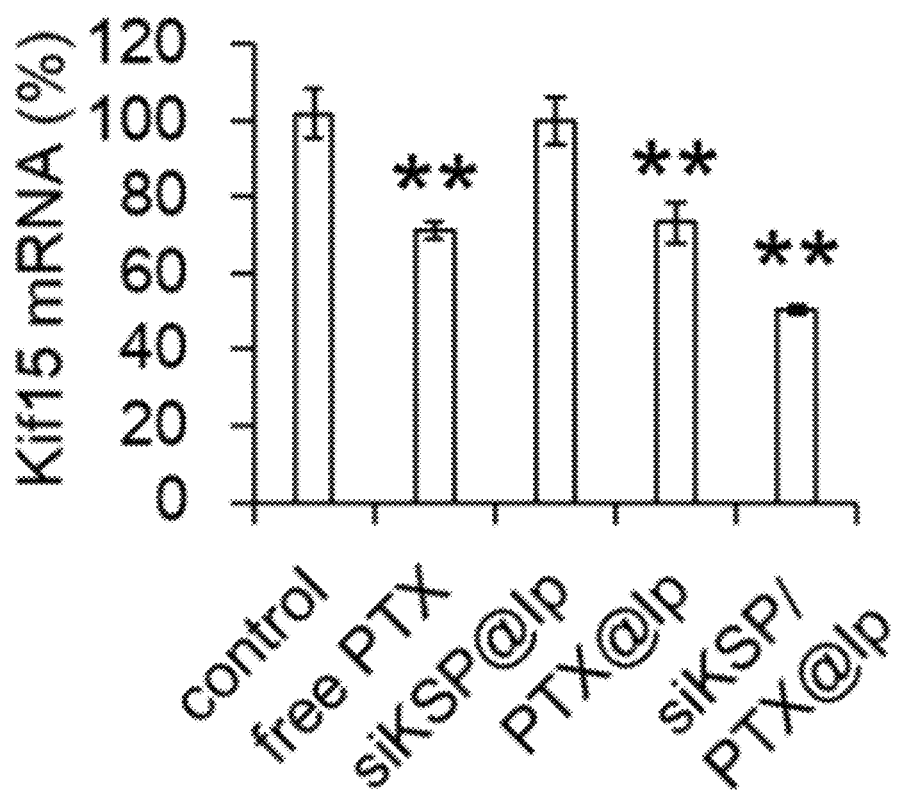
FIG. 2C is a graph illustrating results of comparison among expression levels of a Kif15 gene in HeyA8-MDR cells showing changes by treatment with the KSP siRNA/PTX-liposome.

Thereafter, the levels of the amplified products obtained from the PCR were measured, and the measured levels were standardized with respect to an expression amount of β-actin, and then relative levels of Kif15 mRNA was calculated (FIG. 2C).

FIG. 2C is a graph illustrating results of comparison among expression levels of a Kif15 gene in HeyA8-MDR cells showing changes by treatment with the KSP siRNA/PTX-liposome.

As shown in FIG. 2C, it was confirmed that the expression level of the Kif15 gene was not changed in the cells by treating the cells with the PEGylated liposome containing only siKSP, but the expression level of the Kif15 gene was inhibited in the cells when the cells were treated with paclitaxel alone or with the paclitaxel-containing PEGylated liposome. In addition, when treating the cells with the PEGylated liposome containing both siKSP and paclitaxel, the expression level of the Kif15 gene was further reduced when compared with the cells treated with paclitaxel alone.

Example 3-4: Inhibitory Effect on Expression of Kif15 at the Protein Level

Figure 2D:
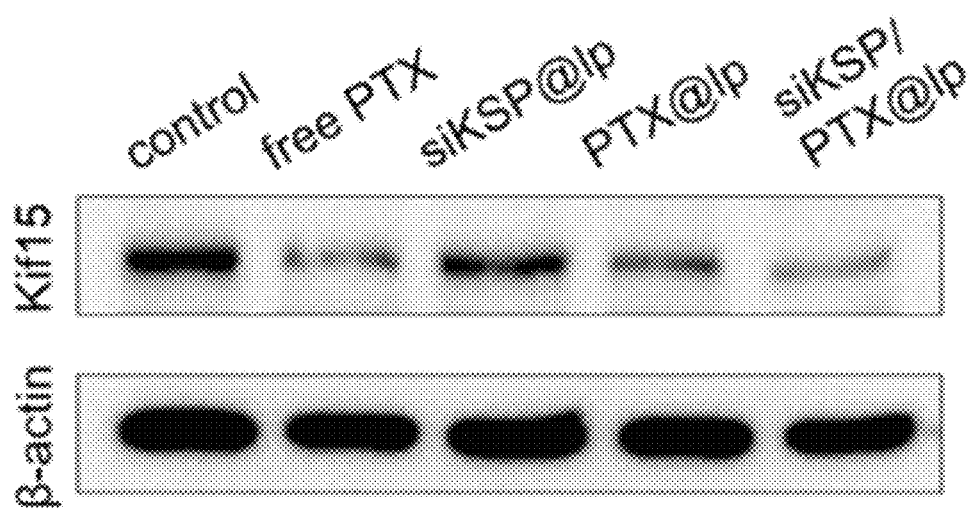
FIG. 2D is a western blot analysis image illustrating results of comparison among levels of a Kif15 protein in HeyA8-MDR cells showing changes by treatment with the KSP siRNA/PTX-liposome.

The cells recovered in Example 3-3 above were analyzed by western blotting using an anti-Kif15 antibody (FIG. 2D).

FIG. 2D is a western blot analysis image illustrating results of comparison among levels of a Kif15 protein in HeyA8-MDR cells showing changes by treatment with the KSP siRNA/PTX-liposome.

As shown in FIG. 2D, it was confirmed that the expression level of the Kif15 protein was not changed in the cells when treating the cells with the PEGylated liposome containing only siKSP, but the level of the Kif15 protein was decreased in the cells when treating the cells with paclitaxel alone or the paclitaxel-containing PEGylated liposome. In addition, when treating the cells with the PEGylated liposome containing both siKSP and paclitaxel, the level of the Kif15 protein was relatively further reduced when compared with the cells treated with paclitaxel alone.

Example 3-5: Inhibitory Effect on Spindle Formation

First, HeyA8-MDR cells, which had been cultured in a 12-well plate at a density of $1 \times 10^5$ cells/well using an RPMI-1640 medium (supplemented with 10% FBS and 0.1% gentamicin sulfate), were treated respectively with PBS (control; 10 μM), a KSP siKSP/PTX-liposome (siKSP/PTX@Ip; equivalent to 50 nM siKSP and 2000 nM PTX), a paclitaxel-containing PEGylated liposome (PTX@Ip; equivalent to 2000 nM PTX), a KSP siRNA-containing PEGylated liposome (siKSP@Ip; equivalent to 50 nM siKSP) or a mixture of siKSP and a PEGylated liposome (scKSP@Ip; equivalent to 50 nM siKSP) for 2 hours, and then the cells recovered.

Subsequently, the recovered cells were washed with a PBS buffer and further cultured in a fresh RPMI-1640 medium for 34 hours. Thereafter, the cells were immobilized with 4% (w/v) paraformaldehyde, treated with 0.25% Triton X-100, and blocked with BSA for 1 hour at room temperature. Subsequently, the cells were immunostained with an anti-α-tubulin antibody and stained with an Alexa Fluor 488 anti-mouse secondary antibody (Cell Signaling Technology) and DAPI, followed by observation using a confocal microscope (FIG. 2E).

Figure 2E:
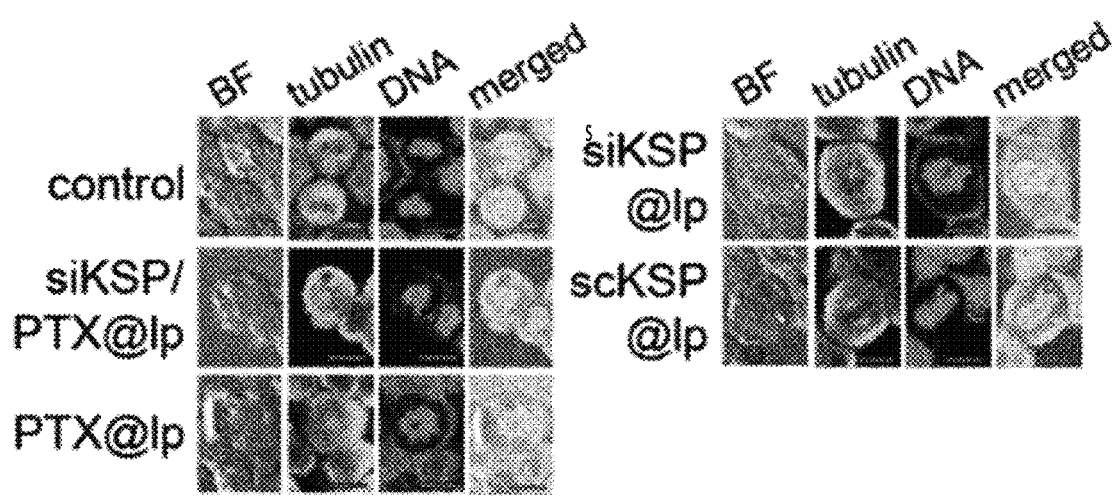
FIG. 2E shows confocal microscope images of HeyA8-MDR cells illustrating results of comparison among spindle shapes in the cells to identify the effect of the KSP siRNA/PTX-liposome.

FIG. 2E shows confocal microscope images of HeyA8-MDR cells illustrating results of comparison among spindle shapes in the cells showing changes by treatment with the KSP siRNA/PTX-liposome.

As shown in FIG. 2E, while normal bipolar spindle assemblies were observed in the cells when the cells were treated with the PBS or the mixture of siKSP and the PEGylated liposome, formation of abnormal monoastral spindles was confirmed when the cells were treated with the PEGylated liposome selectively containing siKSP or paclitaxel.

Example 3-6: Inhibitory Effect on Cancer Cell Division

First, HeyA8-MDR cells, which had been cultured in a 6-well plate at a density of $1 \times 10^5$ cells/well using an RPMI-1640 medium (supplemented with 10% FBS and 0.1% gentamicin sulfate) for 24 hours, were treated respectively with a combination of a KSP siRNA-containing PEGylated liposome (siKSP@Ip; equivalent to 50 nM siKSP) and 10 μM Kif15-IN-1 (Kif15 inhibitor) for 4 hours; or with a combination of a KSP siRNA-containing PEGylated liposome (siKSP@Ip; equivalent to 50 nM siKSP) and paclitaxel (PTX; equivalent to 2000 nM PTX) for 4 hours, and then the cells were recovered. In this case, the cells treated with PBS (control; 10 μM) were used as a control.

Subsequently, the recovered cells were washed with a PBS buffer, and further cultured in a fresh RPMI-1640 medium for 5 days.

Thereafter, the cultured cells were immobilized with 4% (w/v) paraformaldehyde, and stained with a crystal violet solution (0.5%). Then, staining levels of colonies were compared using the Minibis Bioimaging system (DNR Bio-Imaging Systems Ltd., Israel) (FIG. 2F).

Figure 2F:
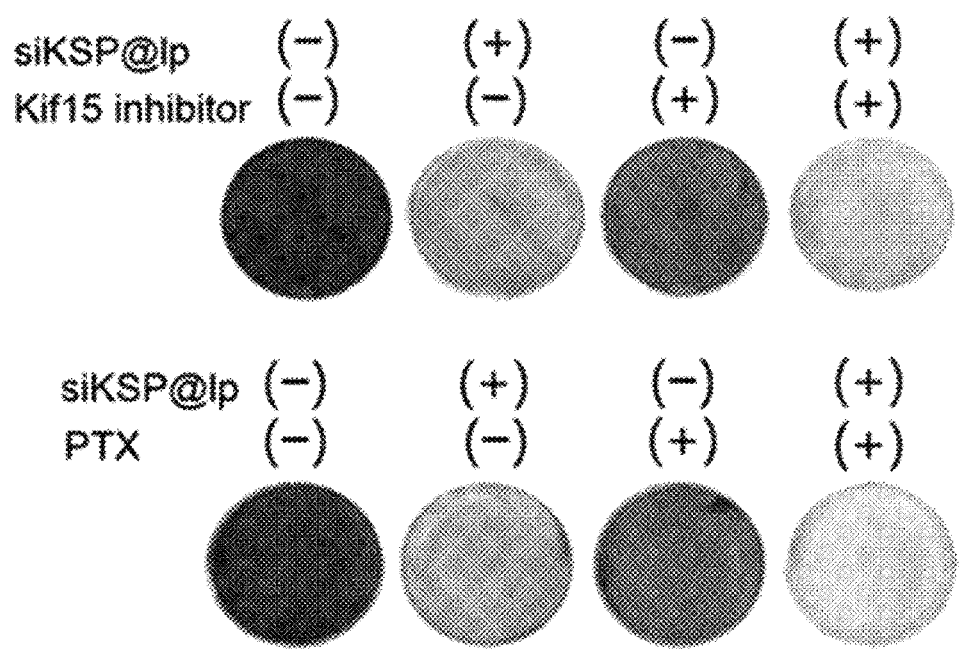
FIG. 2F shows photographs illustrating results of comparison of cell division inhibition levels in HeyA8-MDR cells by treatment of a combination of KSP siRNA and a Kif15 inhibitor and a combination of KSP siRNA and paclitaxel.

FIG. 2F shows photographs illustrating results of comparison of cell division inhibition levels in HeyA8-MDR cells by treatment of a combination of KSP siRNA and the Kif15 inhibitor and a combination of KSP siRNA and paclitaxel.

As shown in FIG. 2F, it was confirmed that cell division was significantly inhibited when treating the cells with the combination of KSP siRNA and the Kif15 inhibitor in comparison with when treating the cells with either KSP siRNA or the Kif15 inhibitor. In addition, it was confirmed that cell division was significantly inhibited when treating the cells with the combination of KSP siRNA and paclitaxel in comparison with when treating the cells with either KSP siRNA or paclitaxel.

Therefore, it can be seen that paclitaxel and the Kif15 inhibitor have the same effect on cancer cell division.

Example 3-7: Anti-Cancer Activity

First, HeyA8-MDR cells, which had been cultured in a 6-well plate at a density of 1×10⁵ cells/well using an RPMI-1640 medium (supplemented with 10% FBS and 0.1% gentamicin sulfate) for 24 hours, were treated with various concentrations (0 to 200 nM) of the KSP siRNA-containing PEGylated liposome (siKSP@Ip; equivalent to 50 nM siKSP) or various concentrations (0 to 2000 nM) of paclitaxel (PTX; equivalent to 2000 nM PTX) for 48 hours, and then the cells were recovered. The recovered cells were cultured in a fresh medium supplemented with a 10% MTT solution for 3 hours and formazan crystals generated by treatment with a Sorensen's glycine buffer and DMSO was dissolved therein. Thereafter, the absorbance thereof was measured at 570 nm and the cell viability was calculated using the same (FIG. 2G).

Figure 2G:
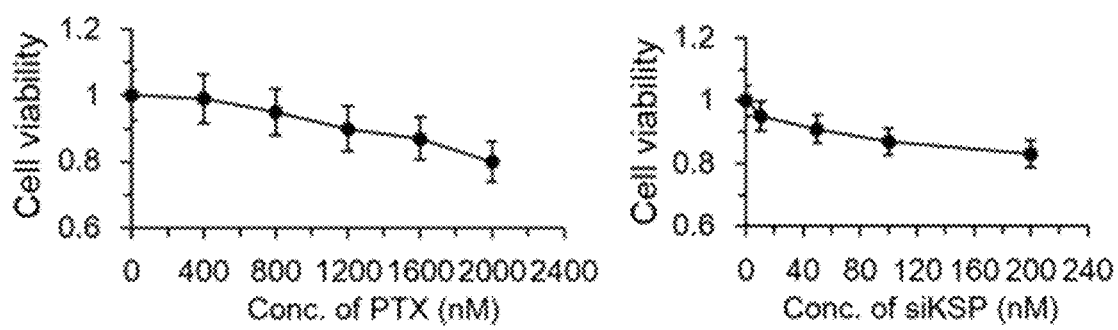
FIG. 2G shows graphs illustrating changes in cell viability of HeyA8-MDR cells with respect to concentrations of the KSP siRNA-containing PEGylated liposome and paclitaxel.

FIG. 2G shows graphs illustrating changes in cell viability of HeyA8-MDR cells with respect to concentrations of the KSP siRNA-containing PEGylated liposome and paclitaxel.

As shown in FIG. 2G, it was confirmed that the cell viability decreases as the concentration of the KSP siRNA-containing PEGylated liposome or paclitaxel increases.

Based on the results above, it can be seen that the KSP siRNA-containing PEGylated liposome or paclitaxel has an anti-cancer activity.

Then, attempts were made to identify whether the KSP siRNA-containing PEGylated liposome and paclitaxel have synergistic anti-cancer effects.

Approximately, the cultured HeyA8-MDR cells were treated with combinations of various concentrations (0 to 100 nM) of the KSP siRNA-containing PEGylated liposome (siKSP@Ip; equivalent to 50 nM siKSP) and various concentrations (0 to 2000 nM) of paclitaxel (PTX; equivalent to 2000 nM PTX) for 48 hours, and then the cells were recovered. The cell viabilities of the cells were compared (FIG. 2H).

Figure 2H:
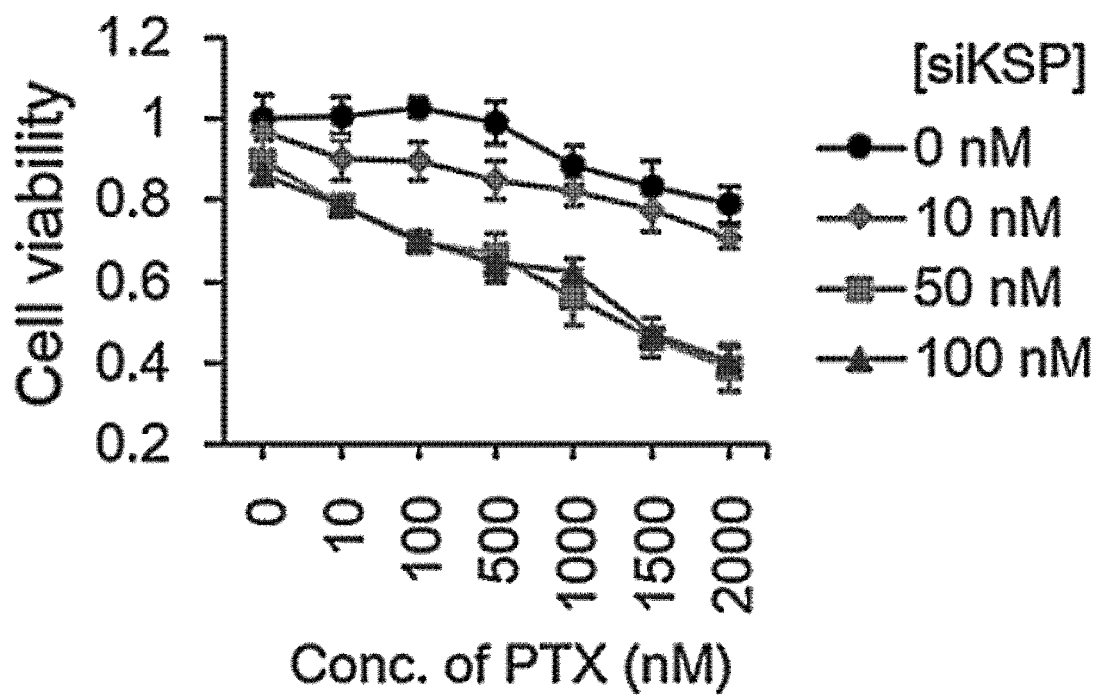
FIG. 2H is a graph illustrating changes in cell viability of HeyA8-MDR cells with respect to concentrations of the KSP siRNA-containing PEGylated liposome and paclitaxel when the cells were simultaneously treated therewith.

FIG. 2H is a graph illustrating changes in cell viability of HeyA8-MDR cells with respect to concentrations of the KSP siRNA-containing PEGylated liposome and paclitaxel when the cells were simultaneously treated therewith.

As shown in FIG. 2H, it was confirmed that the cell viability significantly decreases as the concentrations of the KSP siRNA-containing PEGylated liposome and paclitaxel increase when the cells were simultaneously treated therewith.

In addition, in order to quantitatively analyze a reduction level of the cell viability, the measured absorbance was applied to the following equation to calculate an expected inhibition level of cancer cells, and the obtained expected inhibition level was compared with an observed inhibition level of the cancer cells (FIGS. 2I to 2K). Herein, when the observed inhibition level is higher than the expected inhibition level, it may be understood that synergistic effects are obtained.

$$\text{Expected inhibition level} = F_{siKSP\text{-}liposome} + F_{PTX} - (F_{siKSP\text{-}liposome} \times F_{PTX})$$

In the equation, the 'FsiKSP-liposome' is an apoptosis rate of cancer cells by the KSP siRNA-containing PEGylated liposome among cancer cells not treated with paclitaxel, and the 'FPTX' is an apoptosis rate of cancer cells by paclitaxel among cancer cells not treated with the KSP siRNA-containing PEGylated liposome.

FIG. 2I is a table showing observed inhibition levels of cancer cells according to concentrations of the KSP siRNA-containing PEGylated liposome and paclitaxel in HeyA8-MDR cells when the cells are simultaneously treated therewith. FIG. 2J is a table showing expected inhibition levels of cancer cells according to concentrations of the KSP siRNA-containing PEGylated liposome and paclitaxel in HeyA8-MDR cells when the cells are simultaneously treated therewith. FIG. 2K is a table showing differences between the observed inhibition levels and the expected inhibition levels of cancer cells according to concentrations of the KSP siRNA-containing PEGylated liposome and paclitaxel in HeyA8-MDR cells when the cells are simultaneously treated therewith.

As shown in FIGS. 2I to 2K, it was confirmed that the observed inhibition level was higher than the expected inhibition level when the cells were simultaneously treated with the KSP siRNA-containing PEGylated liposome and paclitaxel.

Therefore, it can be seen that the KSP siRNA-containing PEGylated liposome and paclitaxel have synergistic anti-cancer effects.

Figure 2L:
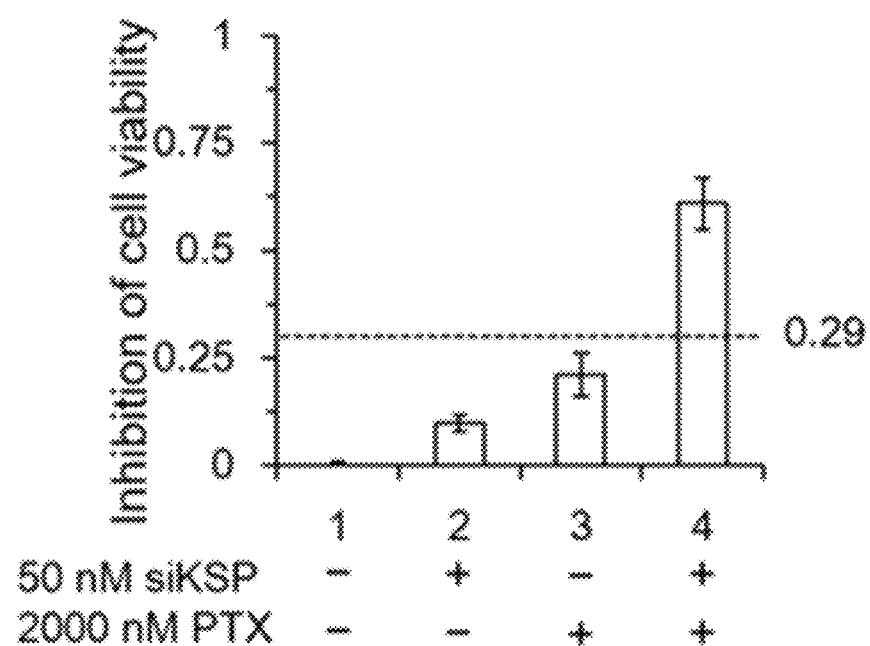
FIG. 2L is a graph showing cell viability inhibition in HeyA8-MDR cells by treatment with a combination of 50 nM KSP siRNA-containing PEGylated liposome and 2000 nM paclitaxel.

Meanwhile, HeyA8-MDR cells, which had been cultured in a 6-well plate at a density of 1×10⁵ cells/well using an RPMI-1640 medium (supplemented with 10% FBS and 0.1% gentamicin sulfate), were treated with a combination of 50 nM KSP siRNA-containing PEGylated liposome (siKSP@Ip; equivalent to 50 nM siKSP) and 2000 nM paclitaxel (PTX; equivalent to 2000 nM PTX) for 48 hours. Thereafter, cell viability inhibition levels and expected inhibition levels calculated therefrom were compared with each other (FIG. 2L). The expected inhibition level is a value obtained using the following equation used in the Bliss independence model below to determine whether the two types of preparations (i.e., KSP siRNA and paclitaxel) have synergistic effects. When there were no synergistic effects, a maximum expected inhibition level was 29% (0.29), which was set as a reference value of the synergistic effects.

$$\text{Expected Inhibition Level} = Fa + Fb - (Fa \times Fb)$$

FIG. 2L is a graph showing cell viability inhibition in HeyA8-MDR cells by treatment with a combination of 50 nM KSP siRNA-containing PEGylated liposome and 2000 nM paclitaxel.

As shown in FIG. 2L, the cell viability inhibition level was 29% or less, which is the reference value of the synergistic effects, when the cells were treated individually with 50 nM KSP siRNA-containing PEGylated liposome or 2000 nM paclitaxel. However, the cell viability inhibition level was about 61.1% when the cells were treated with the combination of 50 nM KSP siRNA-containing PEGylated liposome and 2000 nM paclitaxel, indicating synergistic effects.

Example 3-8: Apoptosis Effect Using FACS Analysis

First, HeyA8-MDR cells, which had been cultured in a 6-well plate at a density of 1×10⁵ cells/well using an RPMI-1640 medium (supplemented with 10% FBS and 0.1% gentamicin sulfate) for 24 hours, were treated respectively with PBS (control; 10 μM), paclitaxel (free PTX; equivalent to 2000 nM PTX), a KSP siRNA-containing PEGylated liposome (siKSP@Ip; equivalent to 50 nM siKSP), a paclitaxel-containing PEGylated liposome (PTX@Ip; equivalent to 2000 nM PTX), and a KSP siKSP/PTX-liposome (siKSP/PTX@Ip; equivalent to 50 nM siKSP and 2000 nM PTX) for 48 hours, and then the cells were recovered. The recovered cells were stained with propidium iodide and FITC-labeled Annexin-V, and analyzed with the Guava easyCyte flow cytometry system (FIG. 2M).

Figure 2M:
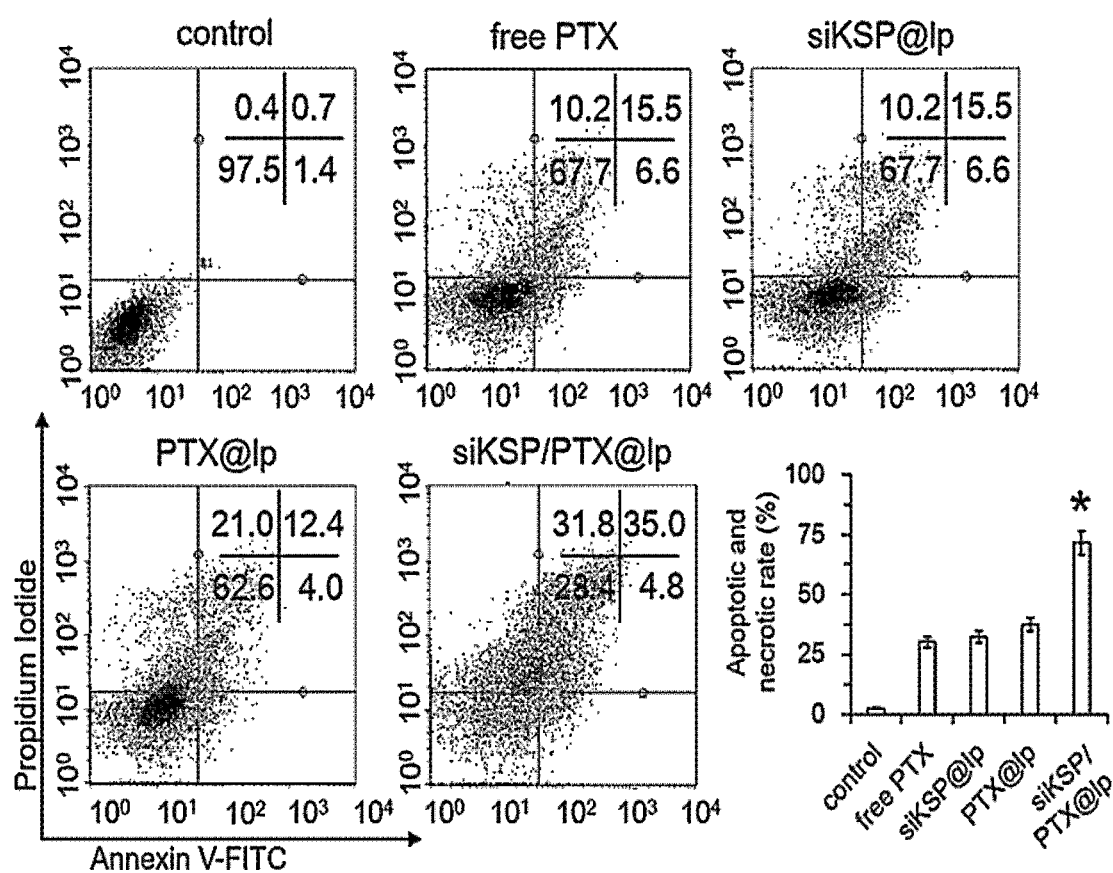
FIG. 2M shows graphs illustrating FACS analysis results indicating apoptosis levels by treatment of the KSP siRNA/PTX-liposome in HeyA8-MDR cells and quantitative analysis results thereof.

FIG. 2M shows graphs illustrating FACS analysis results indicating apoptosis levels by treatment of the KSP siRNA/PTX-liposome in HeyA8-MDR cells and quantitative analysis results thereof.

As shown in FIG. 2M, it was confirmed that apoptosis was induced at low levels when the cells were treated individually with the KSP siRNA-containing PEGylated liposome or the paclitaxel-containing PEGylated liposome, but apoptosis was induced at a very high level when the cells were treated with the KSP siKSP/PTX-liposome.

Example 4: Pharmacological Effect of KSP siRNA/PTX-Liposome Under In Vivo Conditions

Example 4-1: Analysis of Accumulation of Cancer in Mouse Xenograft Model

First, HeyA8-MDR cancer cells ($1 \times 10^8$) were injected into the left thigh of a 5-week-old female BALB/c nude mouse, and then left until cancer tissue grew to a volume of about 200 mm3 to prepare mouse xenograft models.

Subsequently, each mouse was intravenously injected with a fluorescence-labeled Cy5.5-KSP siRNA/oregon-PTX-liposome (1.5 mg/kg) or a fluorescence-labeled Cy5.5-KSP siRNA/oregon-PTX mixture (1.5 mg/kg) via the tail vein of the mouse. After 24 hours, fluorescence signals of Cy5.5 and oregon were measured from the whole body by IVIS Spectrum (Caliper Life Science Inc., USA) (FIG. 3A).

Figure 3A:
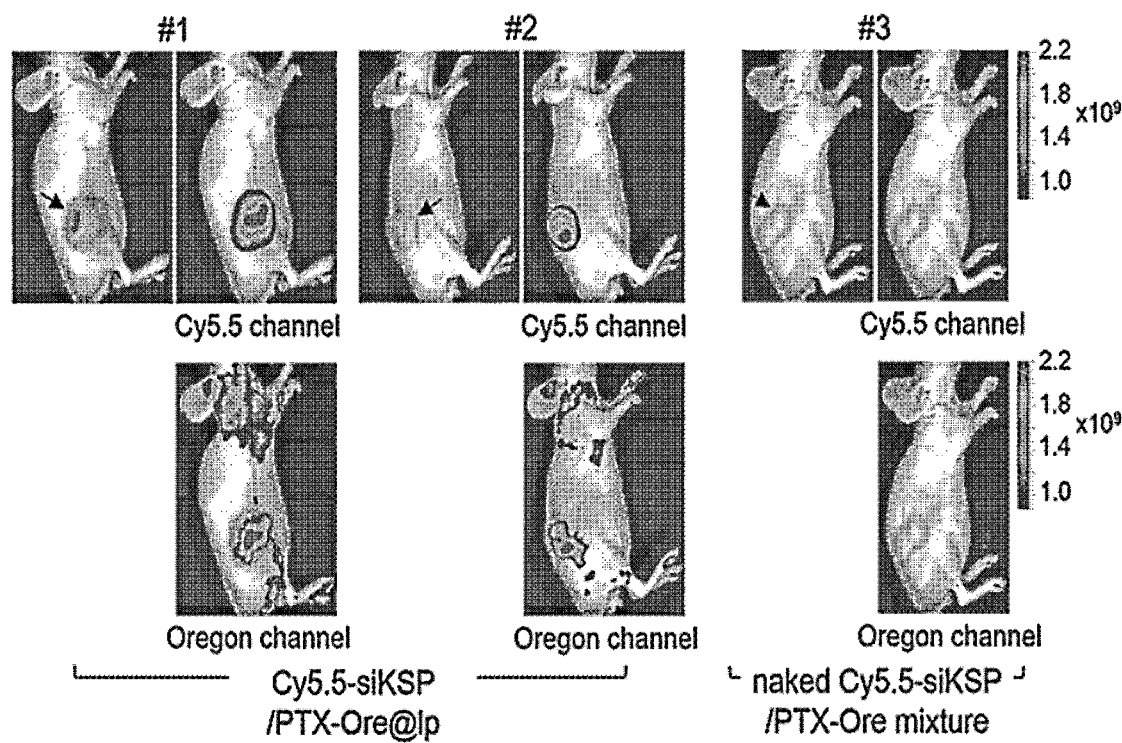
FIG. 3A shows photographs fluorescence signals measured from mouse xenograft models administered with intravenous injection of a fluorescence-labeled liposome.

FIG. 3A shows photographs of fluorescence signals measured from mouse xenograft models administered with intravenous injection of the fluorescence-labeled liposome.

As shown in FIG. 3A, it was confirmed that no fluorescence signal was observed in the model injected with the Cy5.5-KSP siRNA/oregon-PTX mixture, but strong fluorescence signals of each of Cy5.5 and oregon were observed in the tumor tissue injected with the fluorescence-labeled Cy5.5-KSP siRNA/oregon-PTX-liposome.

Then, each of the mice of the mouse xenograft models was sacrificed, and various organs (heart, lung, liver, spleen, and kidney) and tumor tissue were excised therefrom. Fluorescence signals were measured therefrom in the same manner as described above (FIG. 3B).

Figure 3B:
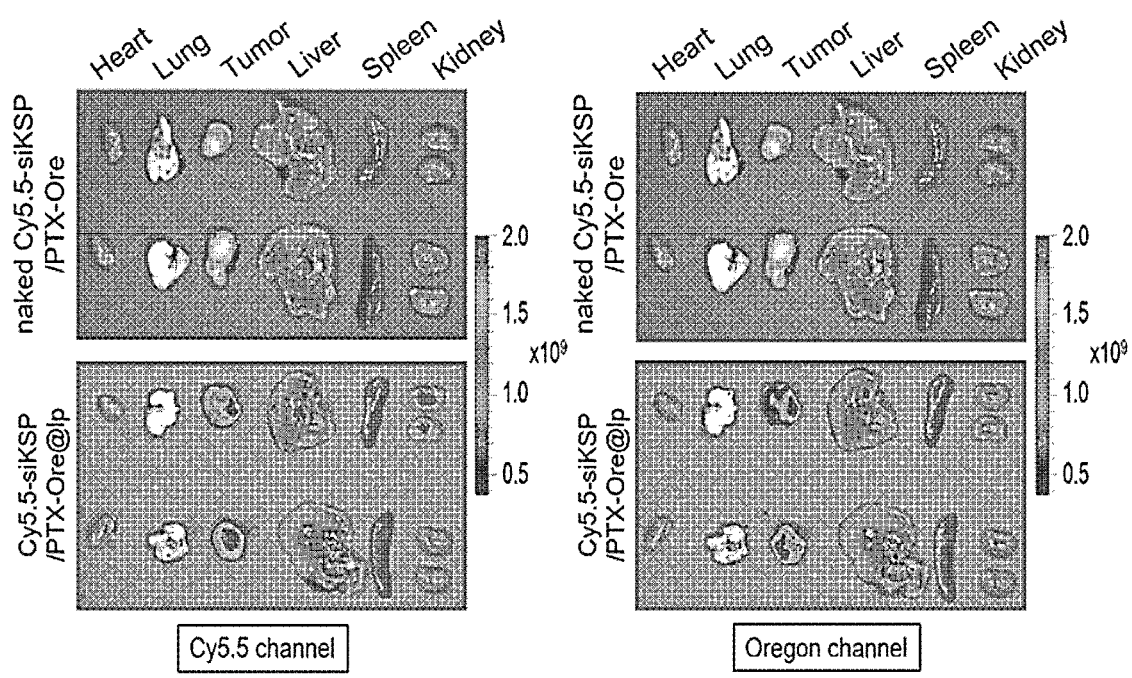
FIG. 3B shows photographs of fluorescence signals measured from organs and tumor tissue excised from mouse xenograft models treated with intravenous injection of a fluorescence-labeled liposome.

FIG. 3B shows photographs of fluorescence signals measured from the organs and tumor tissue excised from the mouse xenograft models treated with intravenous injection of the fluorescence-labeled liposome.

As shown in FIG. 3B, while strong fluorescence signals of Cy5.5 and oregon were observed in the tumor tissue of the mouse treated with injection of the Cy5.5-KSP siRNA/oregon-PTX-liposome, the fluorescence signal was rarely observed in the other organs. In addition, no fluorescence signal was observed in the organs and tumor tissue excised from the mouse treated with injection of the Cy5.5-KSP siRNA/oregon-PTX mixture.

In summary, it can be seen that the Cy5.5-KSP siRNA/oregon-PTX-liposome is effectively accumulated in tumor tissue.

Example 4-2: Anti-Cancer Effect in Tumor Mouse Model

First, HeyA8-MDR cancer cells ($1 \times 10^8$) were injected into the left thigh of a 5-week-old female BALB/c nude mouse, and then left until cancer tissue grew to a volume of about 50 mm3 to prepare 20 tumor mouse xenograft models.

Subsequently, the prepared tumor mouse models were classified into 5 groups below according to samples administered thereto: (i) control (administered with PBS, 0.1 mg/kg, n=4); (ii) free PTX (administered with paclitaxel alone, 2.5 mg/kg, n=4), (iii) siKSP@Ip (administered with the KSP siRNA-containing PEGylated liposome, 0.3 mg/kg for sikSP, n=4); (iv) PTX@Ip (administered with the paclitaxel-containing PEGylated liposome, 2.5 mg/kg for PTX, n=4); and (v) siKSP/PTX@Ip (administered with KSP siKSP/PTX-liposome, 0.3 mg/kg for siKSP and 2.8 mg/kg for PTX, n=4).

Figure 4A:
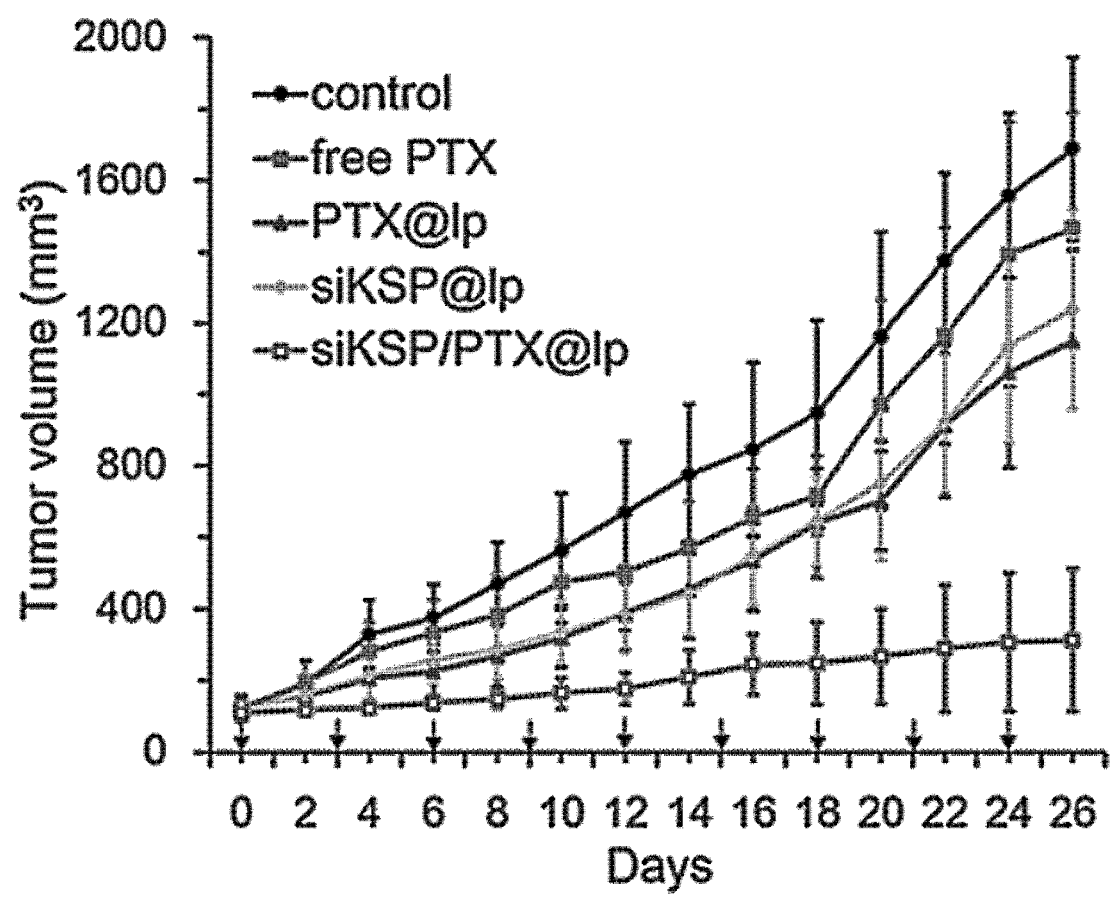
FIG. 4A is a graph showing results of comparison among changes in tumor volume with respect to breeding time of tumor mouse models administered with various samples.

Mice of the respective groups were intravenously injected with each sample via the tail vein of the mice 9 times in total at 3-day intervals, and volumes of tumor were measured at 2-day intervals (FIG. 4A).

FIG. 4A is a graph showing results of comparison among changes in tumor volume with respect to breeding time of tumor mouse models administered with various samples.

As shown in FIG. 4A, it was confirmed that the growth of tumor volume was the most significantly inhibited in the group (v) administered with the KSP siKSP/PTX-liposome when compared with the control, but the growth of tumor volume was inhibited and maintained at lower levels in the group (iii) administered with the KSP siRNA-containing PEGylated liposome or the groups (ii) and (iv) administered with paclitaxel compared with the control.

Figure 4B:
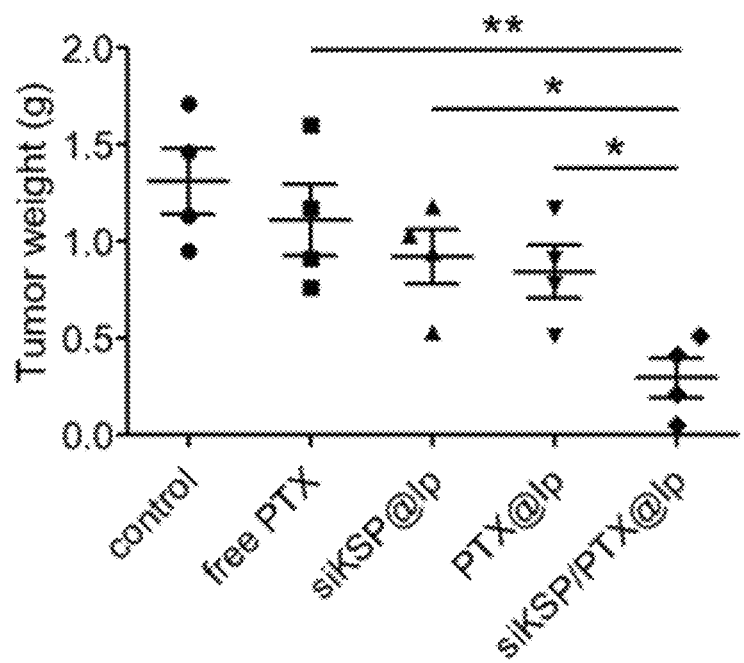
FIG. 4B is a graph showing results of comparison among weight changes in tumor tissue excised from tumor mouse models with respect to breeding time of the tumor mouse models administered with various samples.

Subsequently, at 26 days after injection of each of the samples, tumor tissue was excised from each tumor mouse model and weighed (FIG. 4B).

FIG. 4B is a graph showing results of comparison among weight changes in tumor tissue excised from tumor mouse models with respect to breeding time of the tumor mouse model administered with various samples.

As shown in FIG. 4B, it was confirmed that tumor weight was reduced in the group (v) administered with the KSP siKSP/PTX-liposome by about 77.5% compared to that of the control, reduced in the group (iv) administered with the paclitaxel-containing PEGylated liposome by about 35.8% compared with the control, and reduced in the group (iii) administered with the KSP siRNA-containing PEGylated liposome by about 29.9% compared with the control.

Figure 4C:
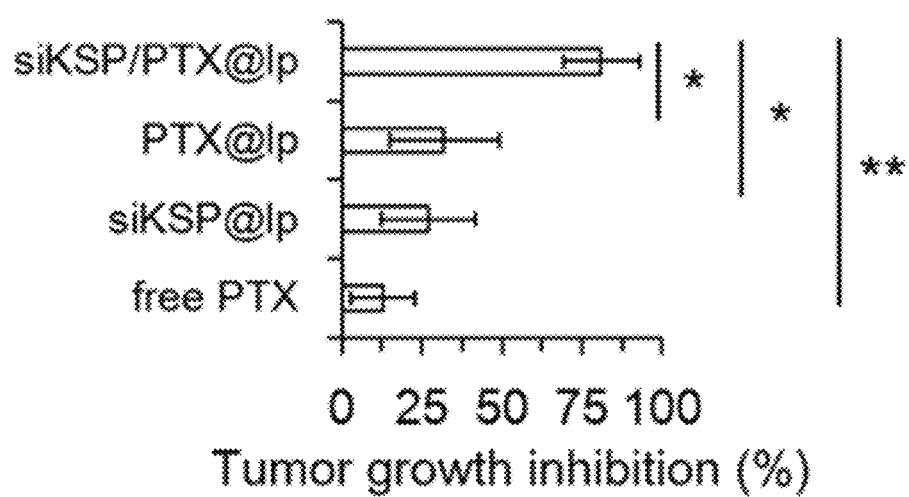
FIG. 4C is a graph showing results of comparison among tumor growth inhibition rates of tumor tissue excised from the tumor mouse models with respect to breeding time of the tumor mouse models administered with various samples.

In addition, at 26 days after injection of each of the samples, tumor tissue was excised from each tumor mouse model, and tumor growth inhibition (TGI) rate was measured (FIG. 4C).

FIG. 4C is a graph showing results of comparison among tumor growth inhibition rates in tumor tissue excised from tumor mouse models with respect to breeding time of the tumor mouse models administered with various samples.

As shown in FIG. 4C, the group (v) administered with the KSP siKSP/PTX-liposome exhibited a TGI value of about 81.2%, the group (iv) administered with the paclitaxel-containing PEGylated liposome exhibited a TGI value of about 32.0%, the group (iii) administered with the KSP siRNA-containing PEGylated liposome exhibited a TGI value of about 27.5%, and the group (ii) administered with paclitaxel alone exhibited a TGI value of about 13.1%.

Example 4-3: Expression Level of Tumor Marker in Tumor Mouse Model

Example 4-3-1: KSP mRNA Level

Figure 4D:
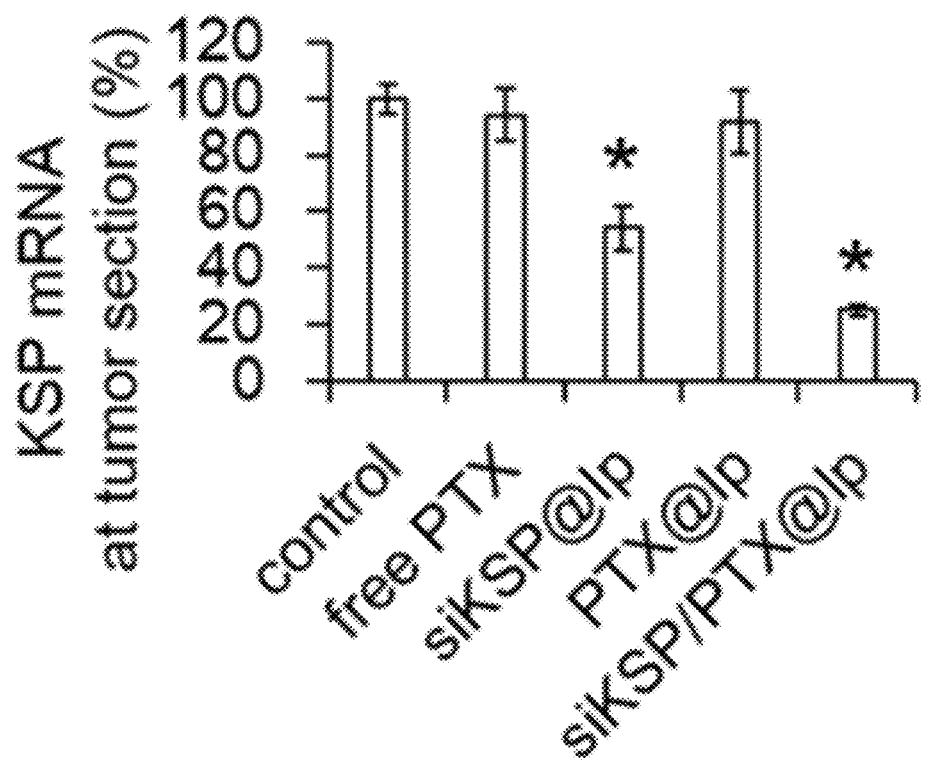
FIG. 4D is a graph showing results of comparison among relative levels of KSP mRNA expressed in tumor tissue of free PTX, siKSP@Ip, PTX@Ip, and siKSP/PTX@Ip groups based on a level of KSP mRNA expressed in tumor tissue of a control in tumor mouse models.

Expression levels of KSP mRNA in tumor tissue of the respective groups excised in Example 4-2 above were measured by qRT-PCR as an application method of that of Example 3-1 (FIG. 4D).

FIG. 4D is a graph showing results of comparison among relative levels of KSP mRNA expressed in tumor tissue of the free PTX, siKSP@Ip, PTX@Ip, and siKSP/PTX@Ip groups based on a level of KSP mRNA expressed in tumor tissue of a control in the tumor mouse models.

As shown in FIG. 4D, it was confirmed that the level of KSP mRNA was decreased only in the groups (iii) and (v) administered with the KSP siRNA-containing PEGylated liposome, and the level of KSP mRNA of the group (v) administered with the PEGylated liposome containing both KSP siRNA and paclitaxel was further decreased more than that of the group (iii) administered with the PEGylated liposome containing KSP siRNA only.

Example 4-3-2: KSP Level

Figure 4E:
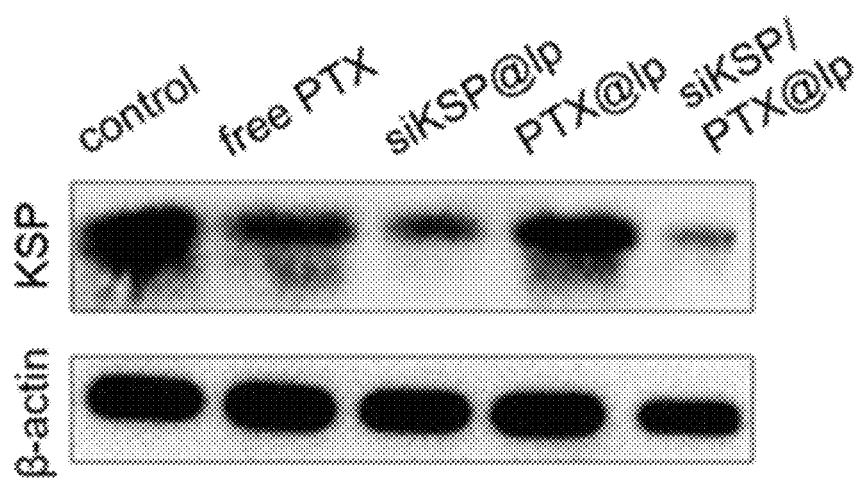
FIG. 4E is a western blot analysis image illustrating results of comparison among KSP levels expressed in tumor tissue of a control and free PTX, siKSP@Ip, PTX@Ip, and siKSP/PTX@Ip groups in tumor mouse models.

KSP levels expressed in tumor tissue of the respective groups excised in Example 4-2 above were measured by the method of Example 3-2 (FIG. 4E).

FIG. 4E is a western blot analysis image illustrating results of comparison among KSP levels expressed in tumor tissue of a control and free PTX, siKSP@Ip, PTX@Ip, and siKSP/PTX@Ip groups in the tumor mouse models.

As shown in FIG. 4E, it was confirmed that the levels of KSP were decreased only in the groups (iii) and (v) administered with the KSP siRNA-containing PEGylated liposome, and the level of KSP of the group (v) administered with the PEGylated liposome containing both KSP siRNA and paclitaxel was further decreased more than that of the group (iii) administered with the PEGylated liposome containing KSP siRNA only.

Example 4-3-3: Ki67 mRNA Level

Figure 4F:
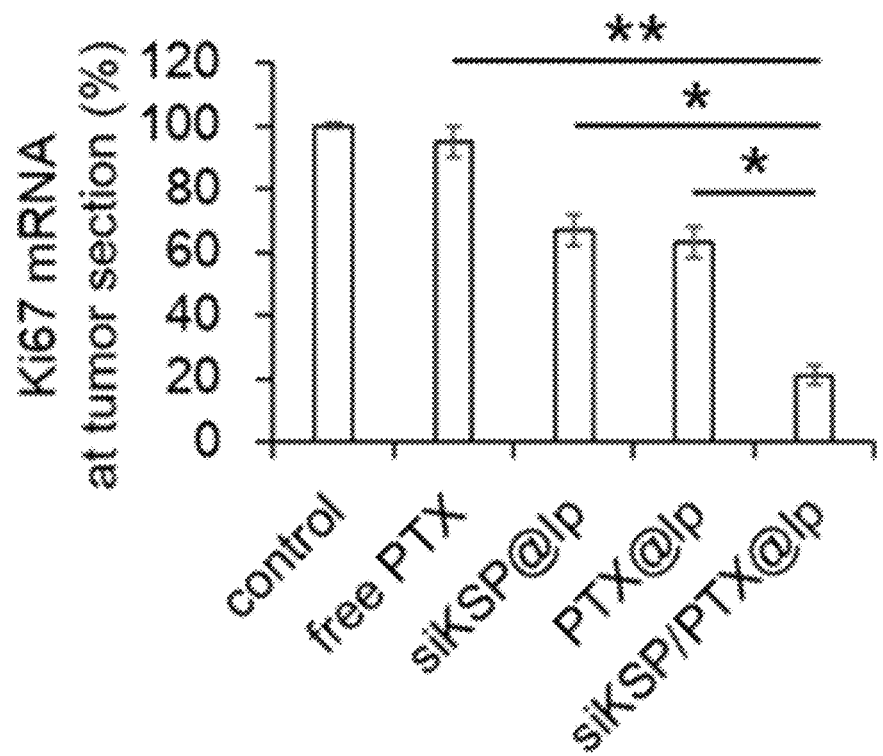
FIG. 4F is a graph showing results of comparison among relative levels of Ki67 mRNA expressed in tumor tissue of free PTX, siKSP@Ip, PTX@Ip, and siKSP/PTX@Ip groups based on a level of Ki67 mRNA expressed in tumor tissue of a control in tumor mouse models.

Levels of Ki67 mRNA, as a cell division marker, expressed in tumor tissue of the respective groups excised in Example 4-2 above were measured (FIG. 4F).

Approximately, total RNA was obtained respectively from the tumor tissue of the respective groups using an RNeasy mini kit (Qiagen, US); KSP cDNA was synthesized from the obtained total RNA using a TOPscript cDNA synthesis kit (Enzynomics, Korea); and PCR was performed using a StepOne qRT-PCR system (Thermo Fisher scientific) and primers specific to a Ki67 gene (SEQ ID NOS: 9 and 10) or primers specific to a β-actin gene (SEQ ID NOS: 5 and 6).

```
Ki67 F:
                                       (SEQ ID NO: 9)
5'-ACGAGACGCCTGGTTACTATC-3'

Ki67 R:
                                       (SEQ ID NO: 10)
5'-GCTCATCAATAACAGACCCATTTAC-3'
```

Then, the levels of the amplified products obtained from the PCR were measured, and the measured levels were standardized with respect to an expression amount of β-actin, and then relative levels of Ki67 mRNA was calculated.

FIG. 4F is a graph showing results of comparison among relative levels of Ki67 mRNA expressed in tumor tissue of the free PTX, siKSP@Ip, PTX@Ip, and siKSP/PTX@Ip groups based on a level of Ki67 mRNA expressed in tumor tissue of a control in the tumor mouse models.

As shown in FIG. 4F, it was confirmed that the levels of Ki67 mRNA were decreased in the groups (iii), (iv), and (v) administered with samples in the form of liposome, and the level of Ki67 mRNA of the group (v) administered with the PEGylated liposome containing both KSP siRNA and paclitaxel was further decreased more than those of the group (iii) administered with the PEGylated liposome containing only KSP siRNA and the group (iv) administered with the PEGylated liposome containing only paclitaxel.

Example 4-3-4: Kif15 mRNA Level

Figure 4G:
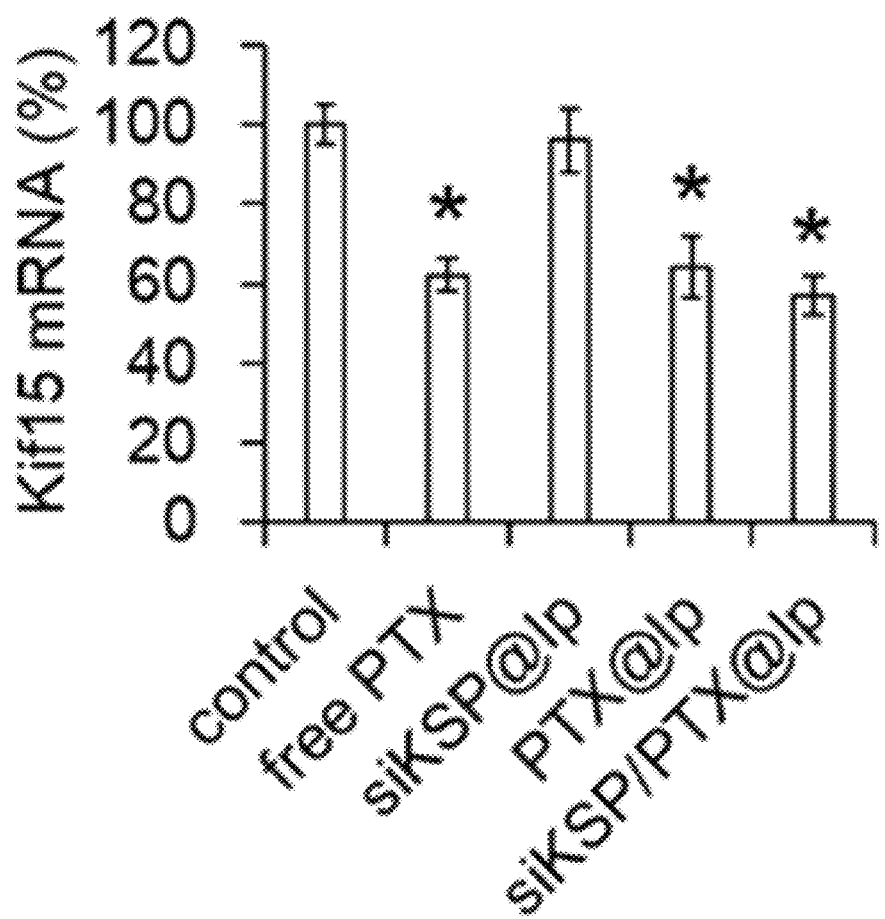
FIG. 4G is a graph showing results of comparison among relative levels of Kif15 mRNA expressed in tumor tissue of free PTX, siKSP@Ip, PTX@Ip, and siKSP/PTX@Ip groups based on a level of Kif15 mRNA expressed in tumor tissue of a control in tumor mouse models.

Expression levels of Kif15 mRNA in tumor tissue of the respective groups excised in Example 4-2 above were measured by qRT-PCR as an application method of that of Example 3-3 (FIG. 4G).

FIG. 4G is a graph showing results of comparison among relative levels of Kif15 mRNA expressed in tumor tissue of the free PTX, siKSP@Ip, PTX@Ip, and siKSP/PTX@Ip groups based on a level of Kif15 mRNA expressed in tumor tissue of a control in the tumor mouse models.

As shown in FIG. 4G, the Kif15 mRNA levels were decreased only in the groups (ii), (iv), and (v) administered with paclitaxel, and there was no significant difference among these three groups.

Example 4-3-5: Immunohistochemistry (IHC)

The cells of tumor tissue of the respective groups excised in Example 4-2 above were immunostained by using a Vectastain universal ABC kit (VECTOR Laboratories).

Approximately, the tumor tissue was immobilized with 10% formalin, embedded into paraffin blocks, and sectioned into 6 μm-thick tissue slices. The obtained tissue slices were washed with a DPBS buffer containing Triton X-100 (0.0125%), blocked with a DPBS buffer containing BSA (1%) for 1 hour, and then treated with an anti-KSP antibody, an anti-Ki67 antibody, or an anti-Kif15 antibody for 12 hours. Subsequently, the resultant was treated with a secondary antibody for 30 minutes, washed with a DPBS buffer, reacted with a Vectastain ABC Reagent for 20 minutes, and allowed to develop colors using 3,3'-diaminobenzidine (DAB) (FIG. 4H).

Figure 4H:
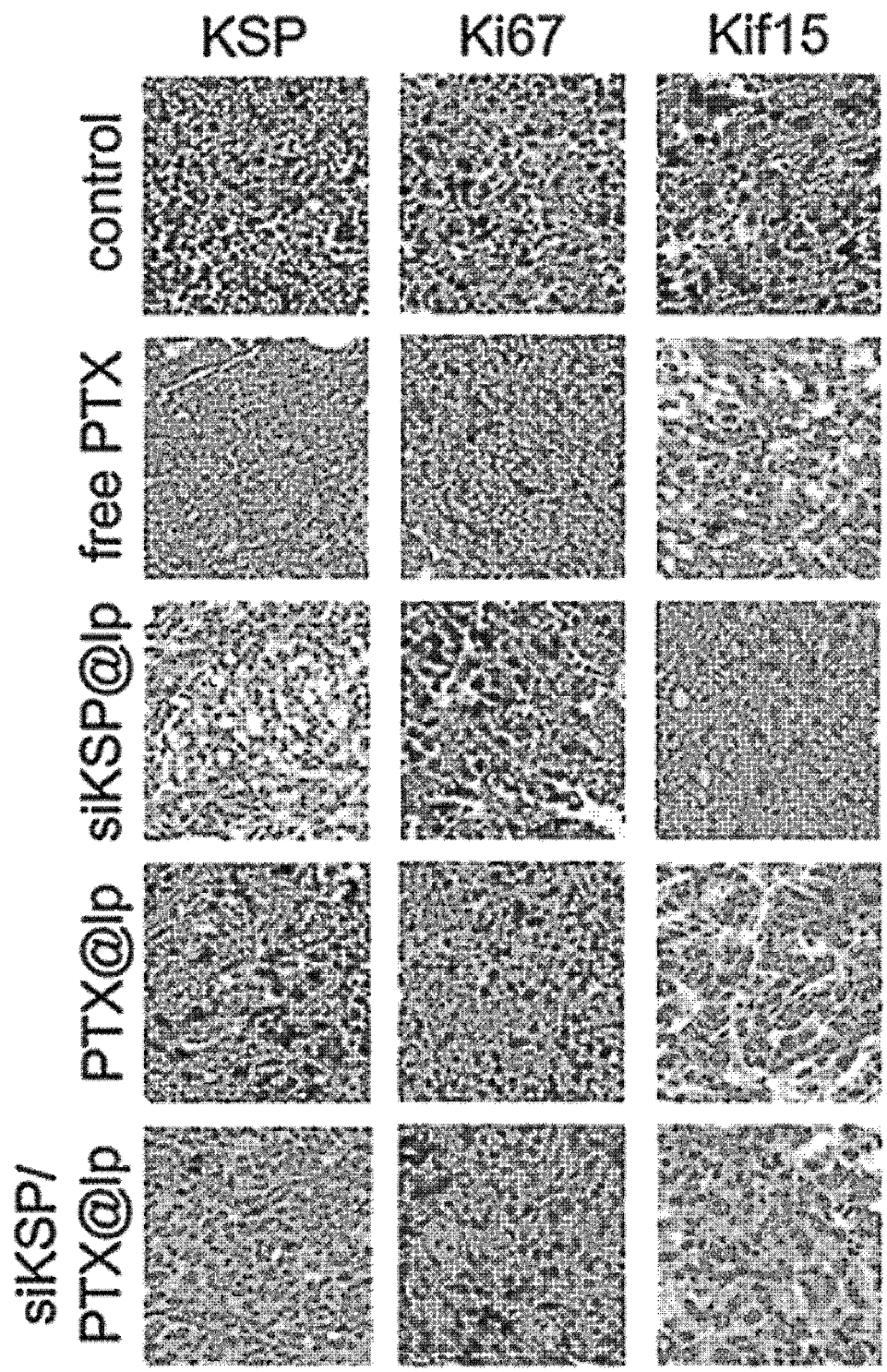
FIG. 4H shows fluorescence microscope images illustrating tumor tissue of a control and free PTX, siKSP@Ip, PTX@Ip, and siKSP/PTX@Ip groups immunostained using anti-KSP antibody, anti-Ki67 antibody, or anti-Kif15 antibody in a tumor mouse model.

FIG. 4H shows fluorescence microscope images illustrating tumor tissue of a control and the free PTX, siKSP@Ip, PTX@Ip, and siKSP/PTX@Ip groups immunostained using an anti-KSP antibody, an anti-Ki67 antibody, and an anti-Kif15 antibody in the tumor mouse models.

As shown in FIG. 4H, it was confirmed that immunostaining results with the anti-KSP antibody are the same as those of FIGS. 4D and 4E, immunostaining results with the anti-Ki67 antibody are the same as those of FIG. 4F, and immunostaining results of the anti-Kif15 antibody are the same as those of FIG. 4G.

Example 4-3-6: TUNEL Assay

Figure 4I:
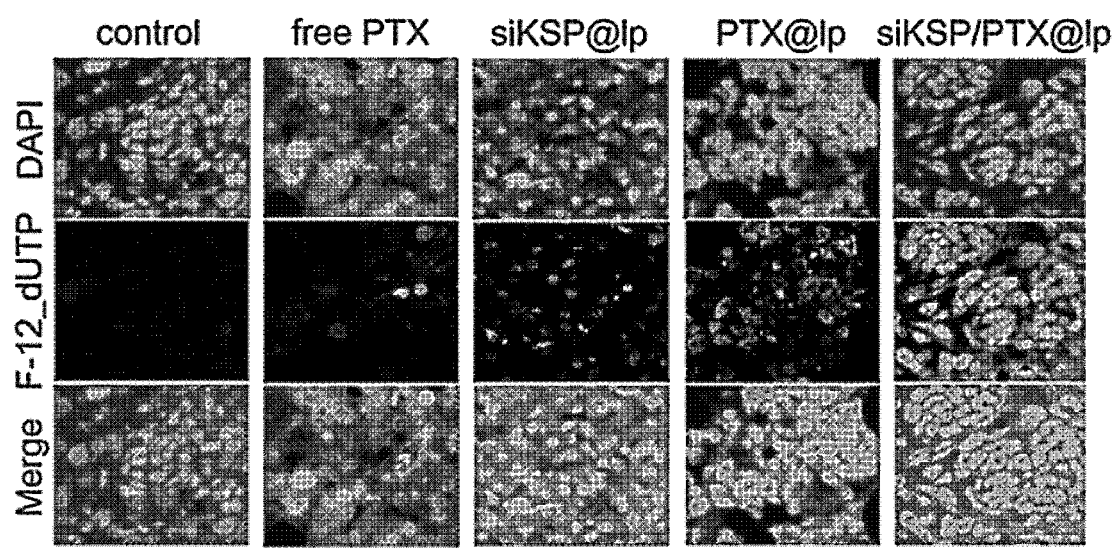
FIG. 4I shows fluorescence microscope images illustrating results of a TUNEL assay performed on tumor tissue of a control and free PTX, siKSP@Ip, PTX@Ip, and siKSP/PTX@Ip groups in tumor mouse models.

The tumor tissue of the respective groups excised in Example 4-2 above was subjected to a TUNEL assay to identify the level of apoptosis in the tumor tissue (FIG. 4I).

FIG. 4I shows fluorescence microscope images illustrating results of the TUNEL assay performed on tumor tissue of a control and the free PTX, siKSP@Ip, PTX@Ip, and siKSP/PTX@Ip groups in the tumor mouse models.

As shown in FIG. 4I, it was confirmed that apoptosis was not induced or induced in a low level in the group (ii) treated with paclitaxel alone, the group (iii) treated with the KSP siRNA-containing PEGylated liposome, or the group (iv) treated with the paclitaxel-containing PEGylated liposome, but apoptosis was induced in a high level in the group (v) administered with the PEGylated liposome containing both KSP siRNA and paclitaxel.

Example 4-4: Anti-Cancer Effect in Drug-Resistant PDX Model

Example 4-4-1: Preparation of Drug-Resistant PDX Model

First, a patient with a drug-resistant tumor was selected. The selected patient had high-grade serious adenocarcinoma (FIGO stage IVB). The patient experienced recurrence of a platinum-resistant tumor during paclitaxel-carboplatin chemotherapy (OV-40, 9 times in total) which was performed for 5 months after primary excision of the tumor.

Then, the tumor collected from the selected patient during a primary debulking surgery was sectioned to a size of 3 mm or less, and then implanted into a subrenal capsule of the left kidney of a mouse to prepare a PDX model.

Example 4-4-2: Anti-Cancer Activity in Drug-Resistant PDX Model

The drug-resistant PDX models prepared in Example 4-4-1 above were classified into 5 groups below according to samples administered thereto: (i) control (administered with PBS, 0.1 mg/kg, n=4); (ii) free PTX (administered with paclitaxel alone, 2.5 mg/kg, n=4); (iii) siKSP@Ip (administered with the KSP siRNA-containing PEGylated liposome, 0.3 mg/kg for sikSP, n=4); (iv) PTX@Ip (administered with the paclitaxel-containing PEGylated liposome, 2.5 mg/kg for PTX, n=4); and (v) siKSP/PTX@Ip (administered with KSP siKSP/PTX-liposome, 0.3 mg/kg for siKSP and 2.8 mg/kg for PTX, n=4).

Mice of the respective groups of the PDX models were intravenously injected with each sample via the tail vein of the mice 9 times in total at 3-day intervals. Tumor tissue was excised from the PDX models at 4 weeks after the first injection (FIG. 5B) and the excised tumor tissue was weighed (FIG. 5A).

Figure 5A:
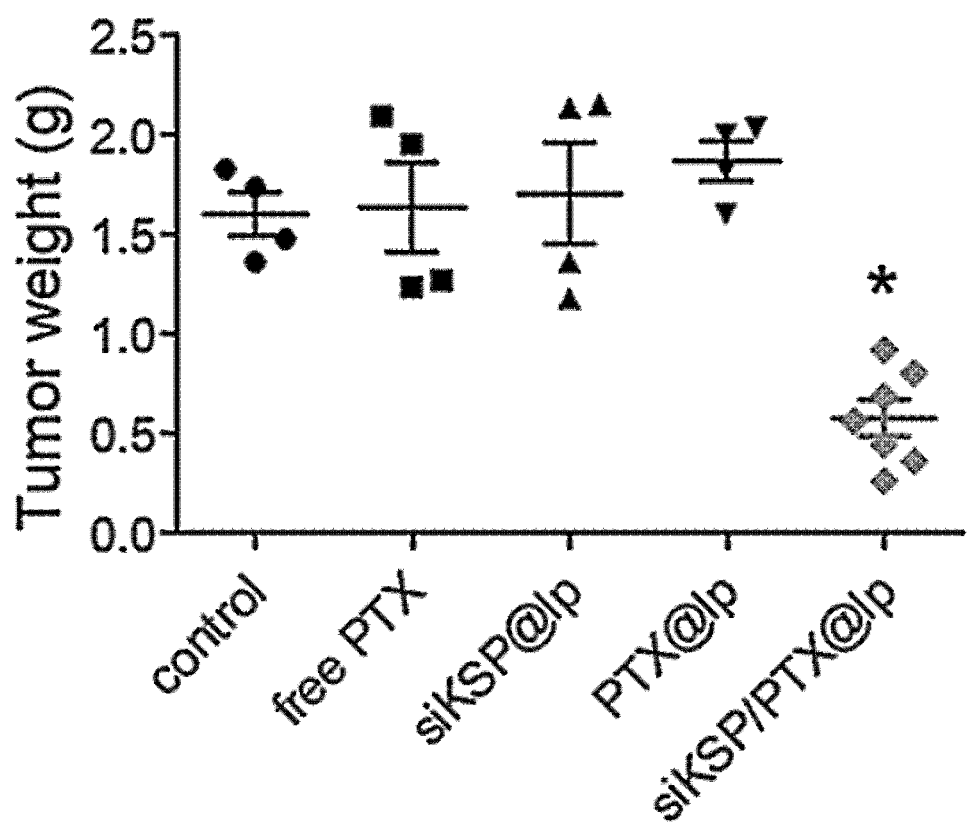
FIG. 5A is a graph showing results of comparison among weights of tumor-implanted kidney tissue excised from a control, and free PTX, PTX@Ip, siKSP@Ip and siKSP/PTX@Ip groups of drug-resistant PDX models.
Figure 5B:
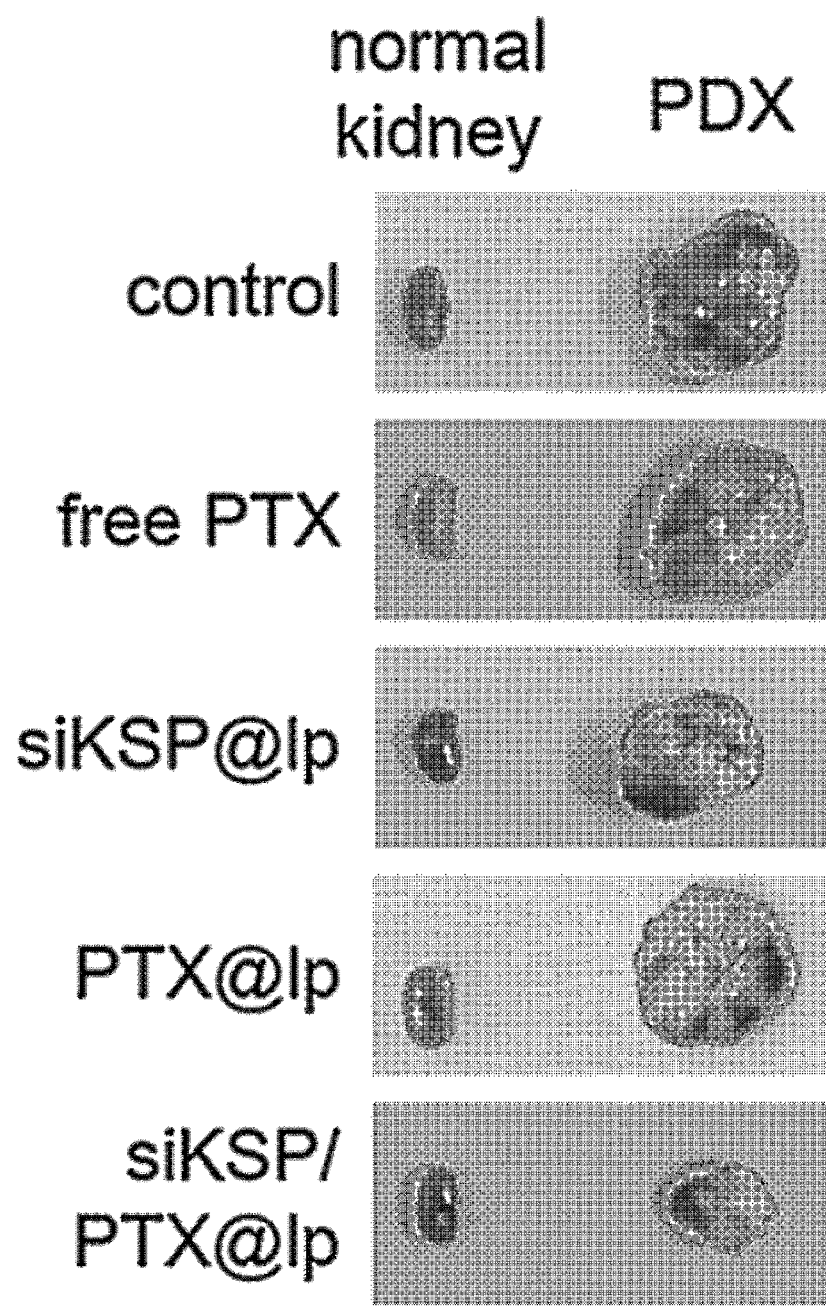
FIG. 5B shows photographs illustrating comparison results of size between a kidney of a normal mouse and the excised tumor-implanted kidneys of the respective groups of drug-resistant PDX models.

FIG. 5A is a graph showing results of comparison among weights of tumor-implanted kidney tissue excised from a control, and the free PTX, PTX@Ip, siKSP@Ip and siKSP/PTX@Ip groups of the drug-resistant PDX models. FIG. 5B shows photographs illustrating comparison results of size between a kidney of a normal mouse and the excised tumor-implanted kidneys of the respective groups of the drug-resistant PDX models.

As shown in FIG. 5A, it was confirmed that the weight of the tumor tissue was significantly decreased in the group (v) administered with the PEGylated liposome containing both KSP siRNA and paclitaxel when compared with the other groups. That is, it was confirmed that the weight of the tumor tissue of the group (v) corresponds to about 33.5% of the weight of the tumor tissue of the group (i), about 35.0% of the weight of the tumor tissue of the group (ii), about 34.5% of the weight of the tumor tissue of the group (iii), and about 29.7% of the weight of the tumor tissue of the group (iv).

Example 4-5: Expression Level of Tumor Marker in Drug-resistant PDX Model

Example 4-5-1: KSP mRNA Level

Figure 5C:
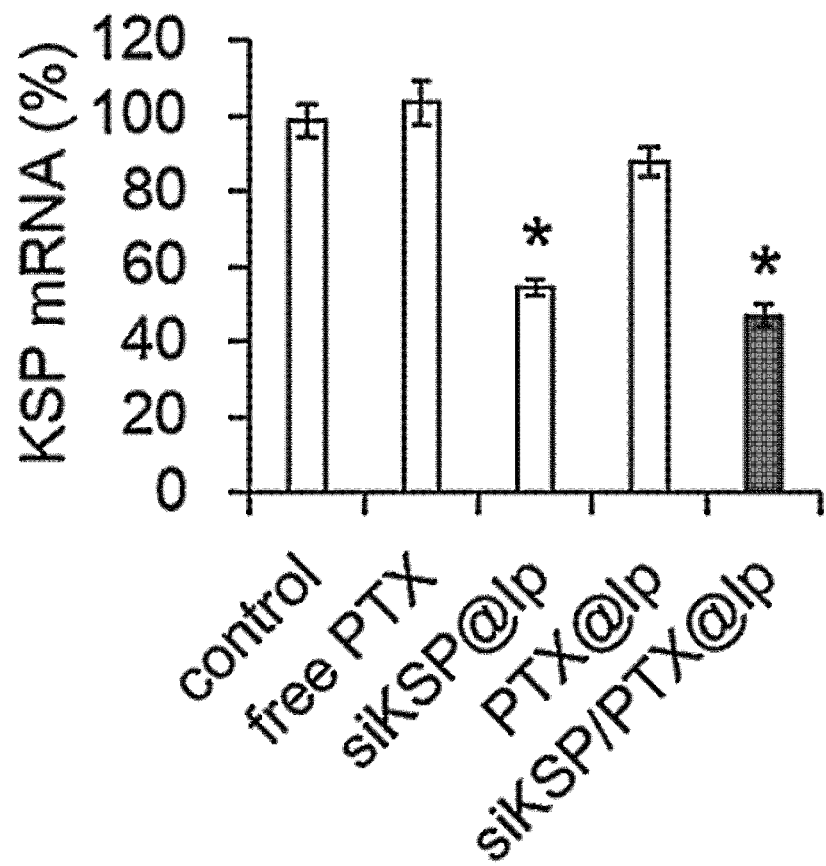
FIG. 5C is a graph showing results of comparison among relative levels of KSP mRNA expressed in tumor-implanted kidney tissue of free PTX, siKSP@Ip, PTX@Ip, and siKSP/PTX@Ip groups based on a level of KSP mRNA expressed in tumor tissue of a control in drug-resistant PDX models.

The levels of KSP mRNA expressed in tumor-implanted kidney tissue of the respective groups excised in Example 4-4-2 above were measured by qRT-PCR as an application method of that of Example 3-1 (FIG. 5C).

FIG. 5C is a graph showing results of comparison among relative levels of KSP mRNA expressed in tumor-implanted kidney tissue of the free PTX, siKSP@Ip, PTX@Ip, and siKSP/PTX@Ip groups based on a level of KSP mRNA expressed in tumor tissue of a control in the drug-resistant PDX models.

As shown in FIG. 5C, it was confirmed that the levels of KSP mRNA were decreased in the groups (iii) and (v) administered with the KSP siRNA-containing PEGylated liposome, and the level of KSP mRNA of the group (v) administered with the PEGylated liposome containing both KSP siRNA and paclitaxel was further decreased more than the group (iii) administered with the PEGylated liposome containing KSP siRNA only.

Example 4-5-2: Ki67 mRNA Level

Figure 5D:
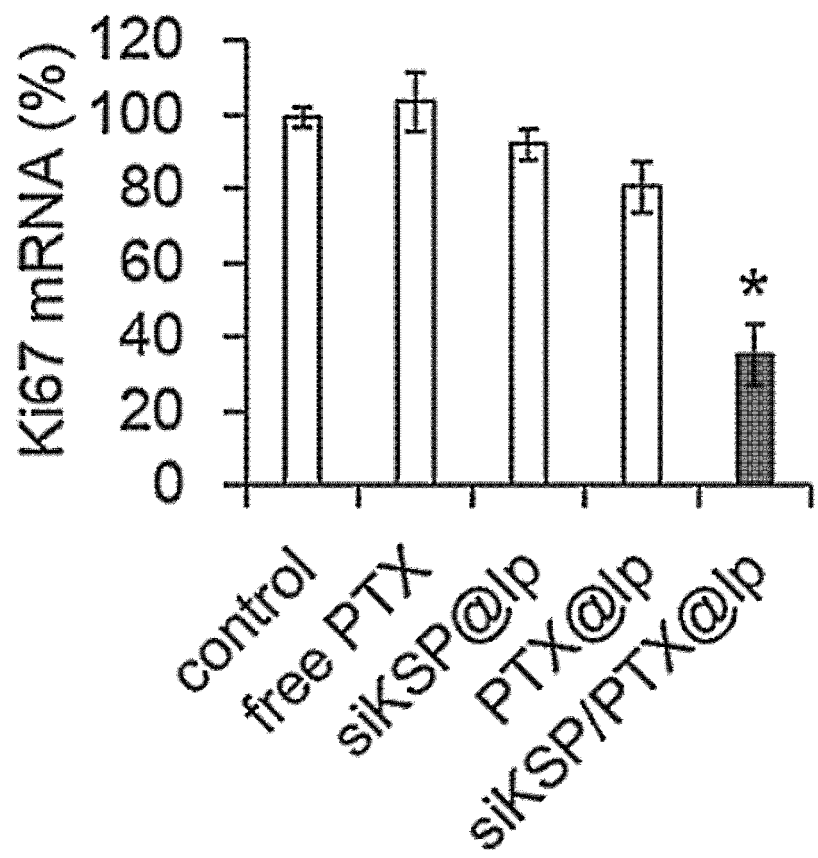
FIG. 5D is a graph showing results of comparison among relative levels of Ki67 mRNA expressed in tumor-implanted kidney tissue of free PTX, siKSP@Ip, PTX@Ip, and siKSP/PTX@Ip groups based on a level of Ki67 mRNA expressed in tumor tissue of a control in drug-resistant PDX models.

The levels of Ki67 mRNA expressed in tumor-implanted kidney tissue of the respective groups excised in Example 4-4-2 were measured according to the method of Example 4-3-3 (FIG. 5D).

FIG. 5D is a graph showing results of comparison among relative levels of Ki67 mRNA expressed in tumor-implanted kidney tissue of the free PTX, siKSP@Ip, PTX@Ip, and siKSP/PTX@Ip groups based on a level of Ki67 mRNA expressed in tumor tissue of a control in the drug-resistant PDX models.

As shown in FIG. 5D, it was confirmed that the levels of Ki67 mRNA were decreased in the groups (iii), (iv), and (v) administered with samples in the form of liposome, and the level of Ki67 mRNA of the group (v) administered with the PEGylated liposome containing both KSP siRNA and paclitaxel was further decreased more than those of the group (iii) administered with the PEGylated liposome containing only KSP siRNA and the group (iv) administered with the PEGylated liposome containing only paclitaxel.

Example 4-5-3: Kif15 mRNA Level

Figure 5E:
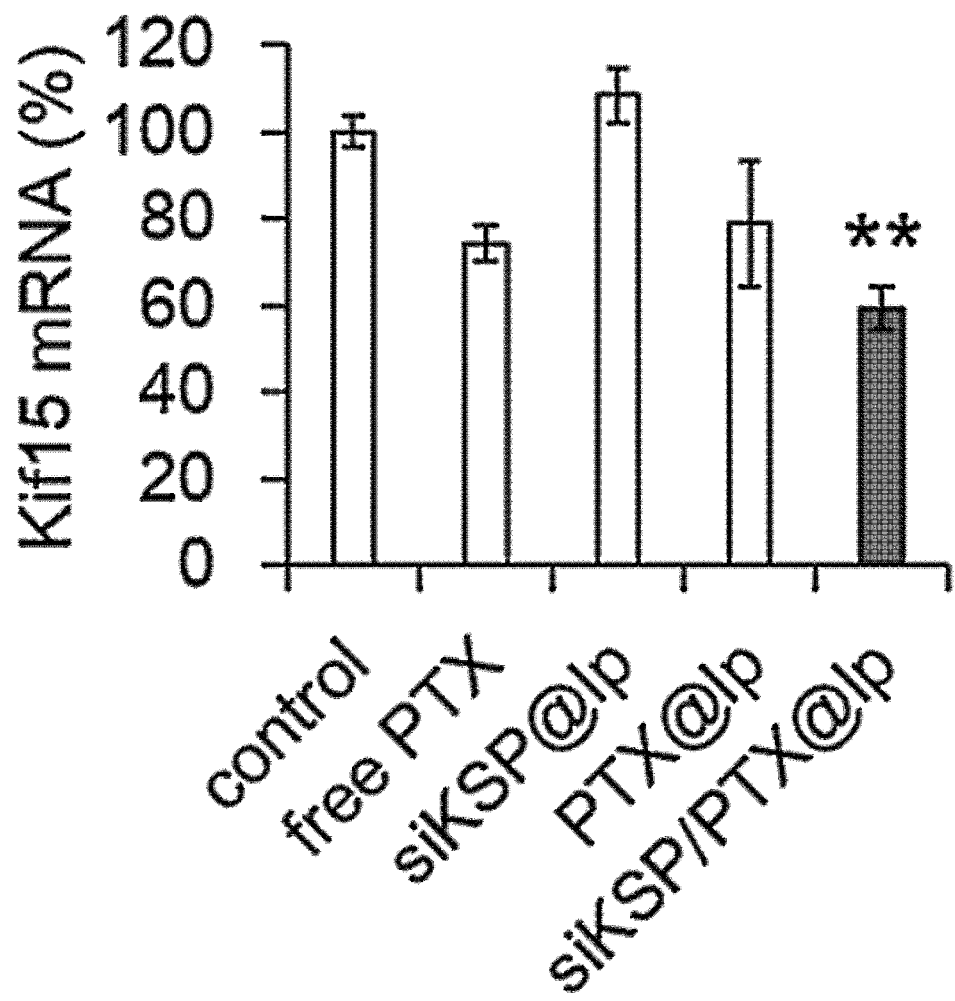
FIG. 5E is a graph showing results of comparison among relative levels of Kif15 mRNA expressed in tumor-implanted kidney tissue of free PTX, siKSP@Ip, PTX@Ip, and siKSP/PTX@Ip groups based on a level of Kif15 mRNA expressed in tumor tissue of a control in drug-resistant PDX models.

The levels of Kif15 mRNA expressed in tumor tissue of the respective groups excised in Example 4-4-2 above were measured by qRT-PCR as an application method of that of Example 3-3 (FIG. 5E).

FIG. 5E is a graph showing results of comparison among relative levels of Kif15 mRNA expressed in tumor-implanted kidney tissue of the free PTX, siKSP@Ip, PTX@Ip, and siKSP/PTX@Ip groups based on a level of Kif15 mRNA expressed in tumor tissue of a control in the tumor mouse models.

As shown in FIG. 5E, it was confirmed that the Kif15 mRNA levels were decreased only in the groups (ii), (iv), and (v) administered with paclitaxel, and the level of Kif15 mRNA in the group (v) administered with the PEGylated liposome containing both KSP siRNA and paclitaxel was further decreased more than the group (ii) administered with paclitaxel and the group (iv) administered with the PEGylated liposome containing only paclitaxel.

Example 4-5-4: KSP Level

Figure 5F:
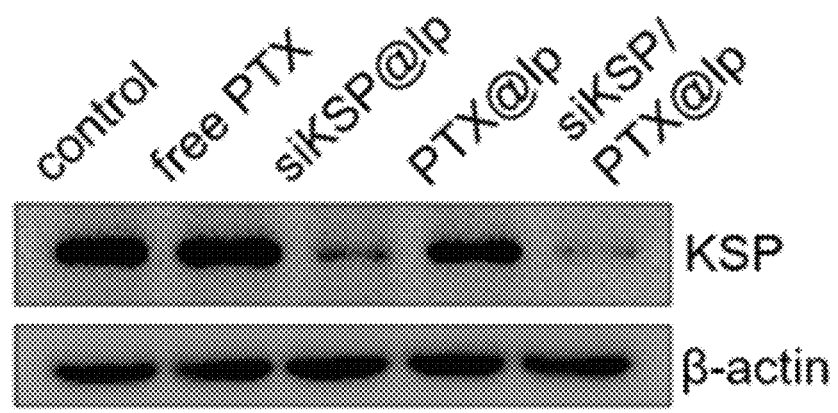
FIG. 5F is a western blot analysis image illustrating results of comparison among KSP levels expressed in tumor-implanted kidney tissue of a control and free PTX, siKSP@Ip, PTX@Ip, and siKSP/PTX@Ip groups in the drug-resistant PDX model.

The levels of KSP expressed in tumor-implanted kidney tissue of the respective groups excised in Example 4-4-2 above were measured by the method of Example 3-2 (FIG. 5F).

FIG. 5F is a western blot analysis image illustrating results of comparison among KSP levels expressed in tumor-implanted kidney tissue of a control and the free PTX, siKSP@Ip, PTX@Ip, and siKSP/PTX@Ip groups in the drug-resistant PDX models.

As shown in FIG. 5F, it was confirmed that the KSP levels were decreased only in the groups (iii) and (v) administered with the KSP siRNA-containing PEGylated liposome, and the level of KSP protein of the group (v) administered with the PEGylated liposome containing both KSP siRNA and paclitaxel was further decreased more than that of the group (iii) administered with the PEGylated liposome containing KSP siRNA only.

Example 4-5-5: Immunohistochemistry (IHC)

Figure 5G:
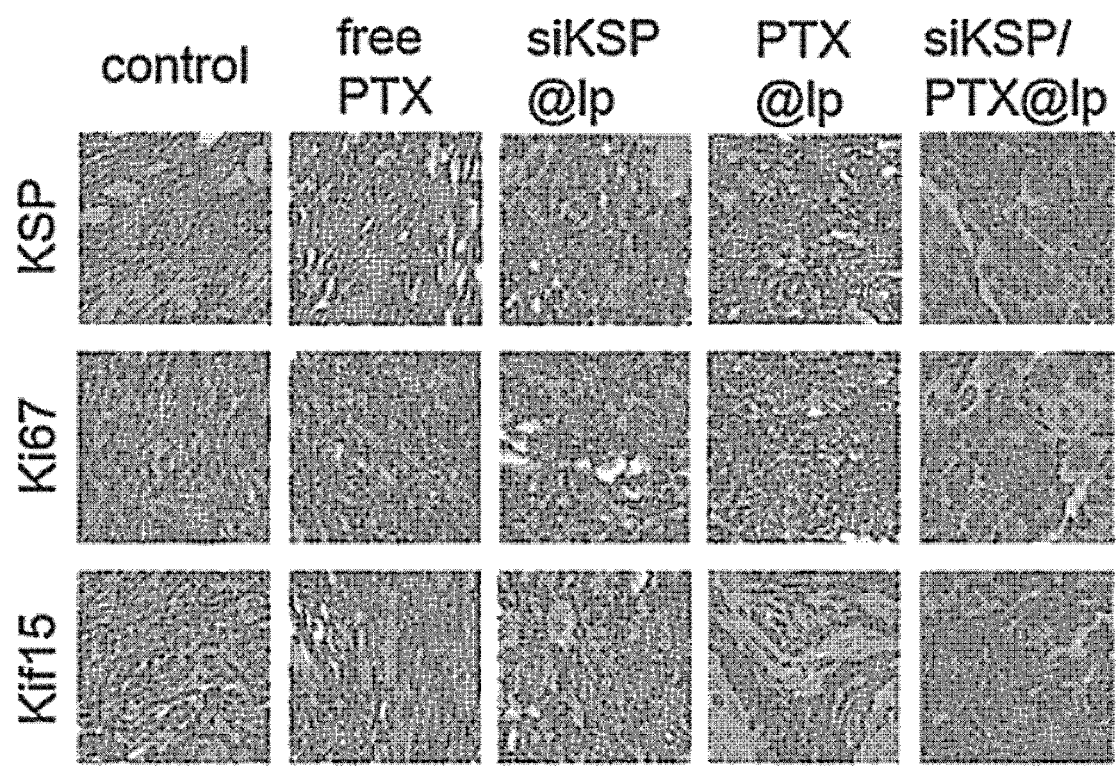
FIG. 5G shows fluorescence microscope images illustrating tumor-implanted kidney tissue of a control and free PTX, siKSP@Ip, PTX@Ip, and siKSP/PTX@Ip groups immunostained using anti-KSP antibody, anti-Ki67 antibody, and anti-Kif15 antibody in drug-resistant PDX models.

The cells of the tumor-implanted kidney tissue of the respective groups excised in Example 4-4-2 above were immunostained according to the method of Example 4-3-5 (FIG. 5G).

FIG. 5G shows fluorescence microscope images illustrating tumor-implanted kidney tissue of a control and the free PTX, siKSP@Ip, PTX@Ip, and siKSP/PTX@Ip groups immunostained using an anti-KSP antibody, an anti-Ki67 antibody, and an anti-Kif15 antibody in the drug-resistant PDX models.

As shown in FIG. 5G, it was confirmed that immunostaining results with the anti-KSP antibody are the same as those of FIGS. 5C and 5F, immunostaining results with the anti-Ki67 antibody are the same as those of FIG. 5D, and immunostaining results of the anti-Kif15 antibody are the same as those of FIG. 5E.

Example 4-5-6: TUNEL Assay

Figure 5H:
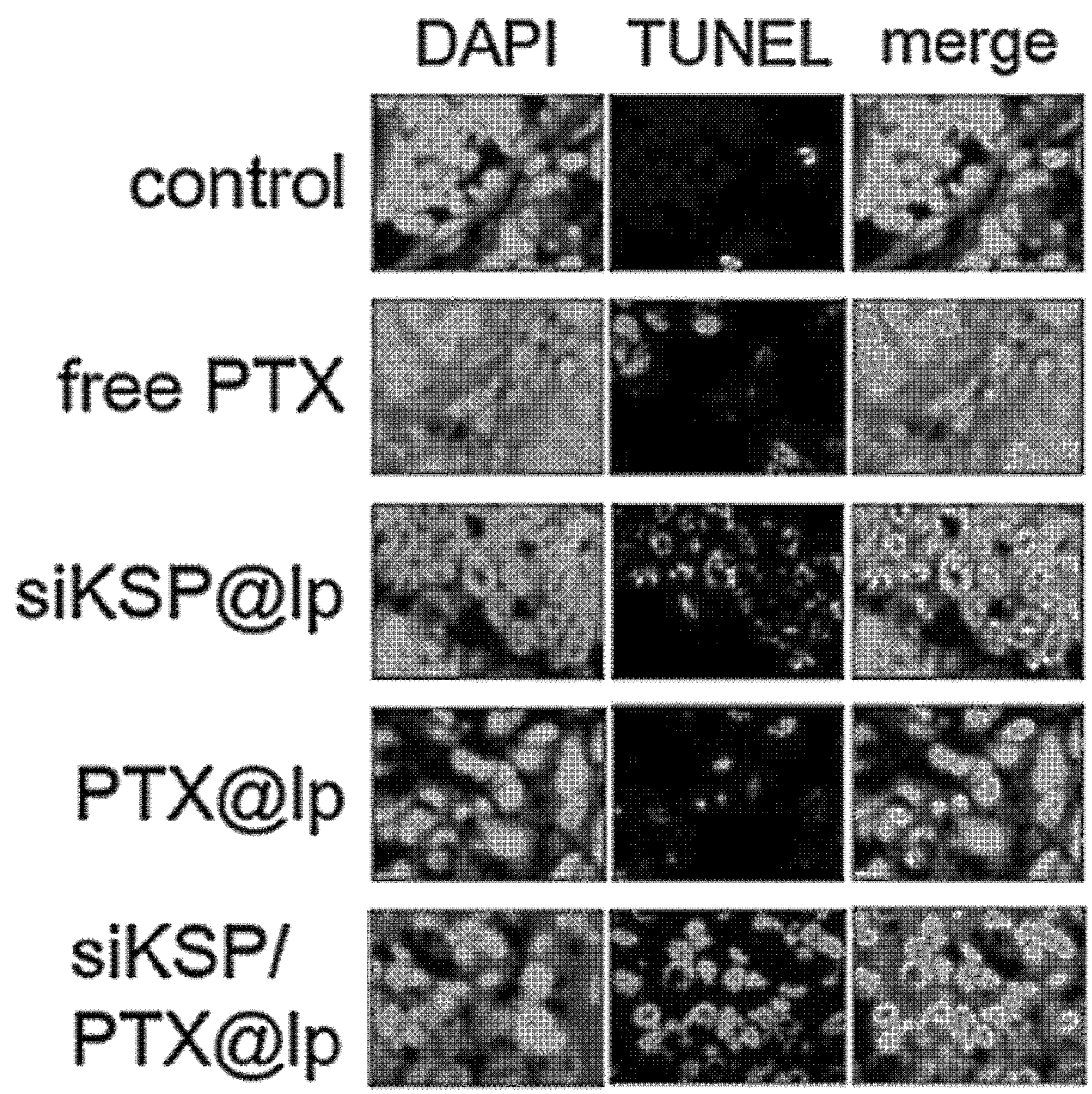
FIG. 5H shows fluorescence microscope images illustrating results of a TUNEL assay performed on tumor-implanted kidney tissue of a control and free PTX, siKSP@Ip, PTX@Ip, and siKSP/PTX@Ip groups in tumor mouse models.

The tumor-implanted kidney tissue of the respective groups excised in Example 4-4-2 above was subjected to a TUNEL assay to identify the level of apoptosis in the tumor-implanted kidney tissue (FIG. 5H).

FIG. 5H shows fluorescence microscope images illustrating results of the TUNEL assay performed on tumor-implanted kidney tissue of a control and the free PTX, siKSP@Ip, PTX@Ip, and siKSP/PTX@Ip groups in the tumor mouse models.

As shown in FIG. 5H, it was confirmed that apoptosis was not induced or induced in a low level in the group (ii) treated with paclitaxel alone, the group (iii) treated with the KSP siRNA-containing PEGylated liposome, or the group (iv) treated with the paclitaxel-containing PEGylated liposome, but apoptosis was induced in a high level in the group (v) administered with the PEGylated liposome containing both KSP siRNA and paclitaxel.

The above description of the present invention is provided for the purpose of illustration, and it would be understood by those skilled in the art that various changes and modifications may be made without changing technical conception and essential features of the present invention. Thus, it is clear that the above-described embodiments are illustrative in all aspects and do not limit the present invention. Therefore, the scope of the disclosure is defined not by the detailed description, but by the claims and their equivalents, and all variations within the scope of the claims and their equivalents are to be construed as being included in the disclosure.

The invention claimed is:

1. A method of treating a cancer, the method comprising administering a pharmaceutical composition to an individual suspected to have the cancer in a pharmaceutically effective amount,
   wherein the pharmaceutical composition comprises a PEGylated liposome, which comprises kinesin spindle protein (KSP) short interfering RNA (siRNA), and a paclitaxel,
   wherein the method simultaneously inhibits expression of KSP and a substitution effect of Kif15 for KSP, by treating kinesin spindle protein (KSP) short interfering RNA (siRNA) and a paclitaxel simultaneously.

2. The method of claim 1, wherein the paclitaxel inhibits a substitution effect of Kif15 for KSP induced when the expression of KSP is inhibited.

3. The method of claim 1, wherein the pharmaceutical composition further comprises a pharmaceutically acceptable carrier, excipient, or diluent.

4. A method of treating a cancer resistant to a cancer therapeutic agent, the method comprising administering a pharmaceutical composition to an individual suspected to have the cancer resistant to the cancer therapeutic agent in a pharmaceutically effective amount, wherein the pharmaceutical composition comprises a PEGylated liposome, which comprises a kinesin spindle protein (KSP) short interfering RNA (siRNA), and a paclitaxel,
   wherein the method simultaneously inhibits expression of KSP and a substitution effect of Kif15 for KSP, by treating kinesin spindle protein (KSP) short interfering RNA (siRNA) and a paclitaxel simultaneously.

5. The method of claim 4, wherein the cancer resistant to the cancer therapeutic agent is a cancer resistant to a cancer therapeutic agent having a mitosis inhibiting activity.

* * * * *